(12) United States Patent
Koga et al.

(10) Patent No.: US 6,654,635 B1
(45) Date of Patent: Nov. 25, 2003

(54) IONTOPHORESIS DEVICE

(75) Inventors: Nobuhiro Koga, Tsukuba (JP);
Hiroyuki Maeda, Tsukuba (JP);
Mitsuru Kuribayashi, Tsukuba (JP);
Naruhito Higo, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 09/622,050

(22) PCT Filed: Feb. 19, 1999

(86) PCT No.: PCT/JP99/00745
§ 371 (c)(1),
(2), (4) Date: Aug. 24, 2000

(87) PCT Pub. No.: WO99/43382
PCT Pub. Date: Sep. 2, 1999

(30) Foreign Application Priority Data

Feb. 25, 1998 (JP) ............................................. 10-060423

(51) Int. Cl.[7] ................................................ A61N 1/30
(52) U.S. Cl. .......................................... 604/20; 604/501
(58) Field of Search ..................................... 604/20, 501

(56) References Cited

U.S. PATENT DOCUMENTS

| | | | | |
|---|---|---|---|---|
| 5,551,597 A | * | 9/1996 | Lambelet et al. | 221/197 |
| 5,795,321 A | * | 8/1998 | McArthur et al. | 604/20 |
| 5,797,867 A | * | 8/1998 | Guerrera et al. | 604/20 |
| 5,817,044 A | * | 10/1998 | Evers et al. | 604/20 |
| 5,837,281 A | * | 11/1998 | Iga et al. | 424/449 |
| 6,355,025 B1 | * | 3/2002 | Phipps et al. | 604/501 |

* cited by examiner

Primary Examiner—J. Casimer Jacyna
(74) Attorney, Agent, or Firm—Townsend & Banta

(57) ABSTRACT

An iontophoresis device, which can ensure the long-term stability of drugs and which can be easily assembled when used, is provided. A donor electrode-printed portion (6) is placed on one side of a backing layer (4), and a reference electrode-printed portion (7) is placed on the other side. Both printed parts are connected to a current generating part (Ia) through a connector (Id). A drug support film (14) is joined to a drug-dissolving portion (11), and a cup-like shaped protective cover (12), which covers the drug support film (14), is removed before the device is used. The exposed drug support film (14) is attached to the skin of a user, and the device is driven by turning on a power supply of the current-generating portion (Ia).

16 Claims, 17 Drawing Sheets

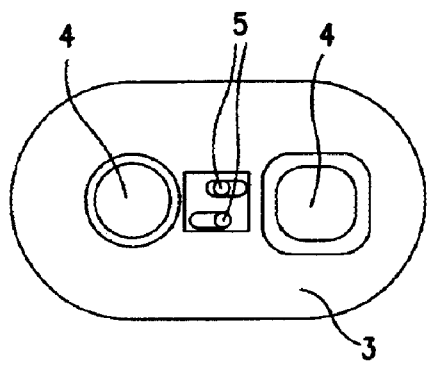
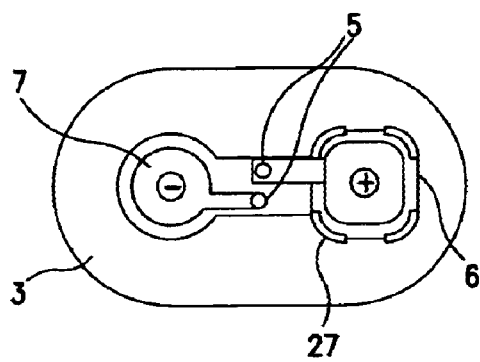
FIG. 4a    FIG. 4b
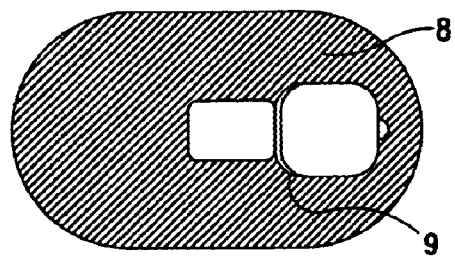
FIG. 4c
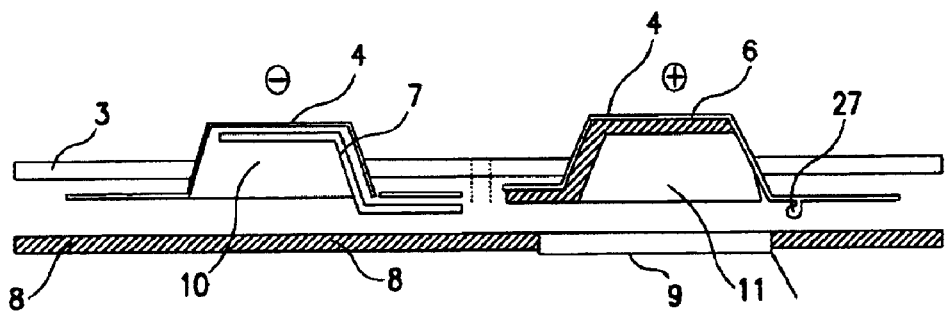
FIG. 4d

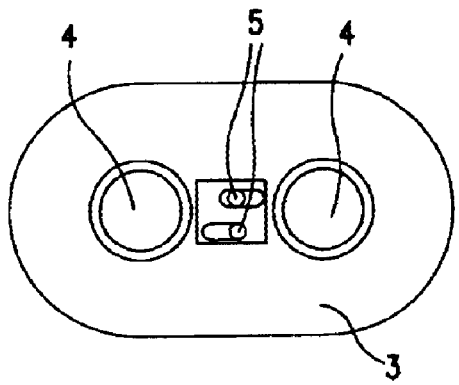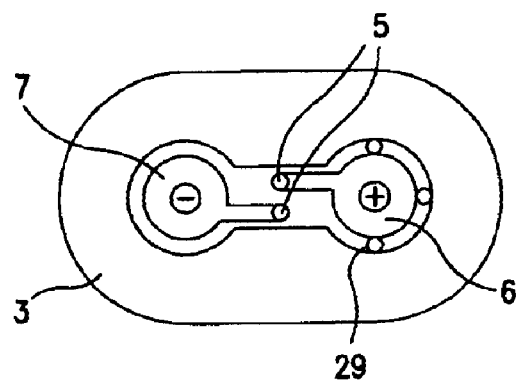
FIG. 8a   FIG. 8b
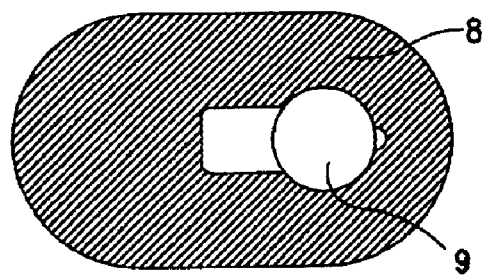
FIG. 8c
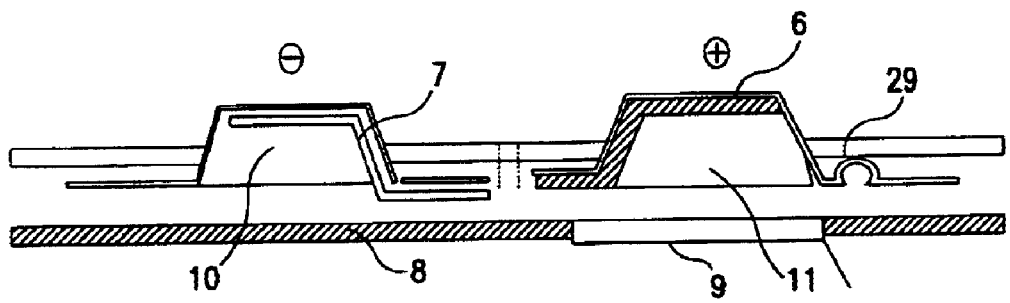
FIG. 8d

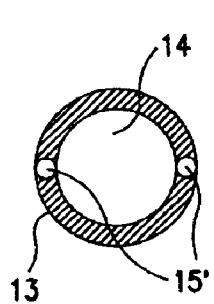 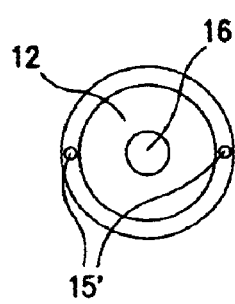 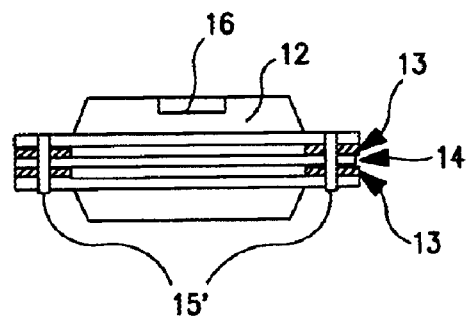
FIG. 11a  FIG. 11b  FIG. 11c
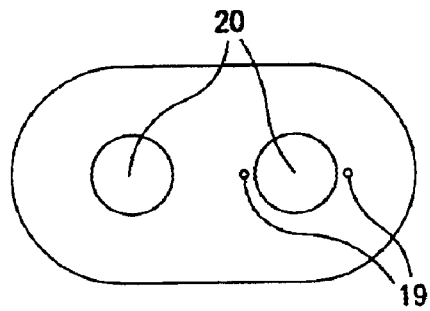 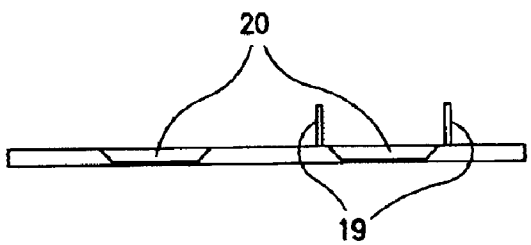
FIG. 12a  FIG. 12b

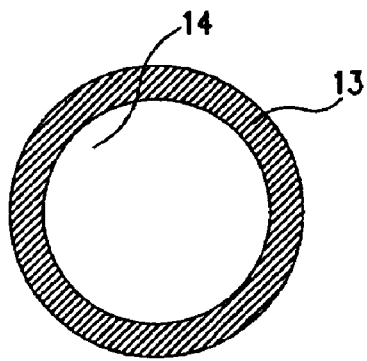
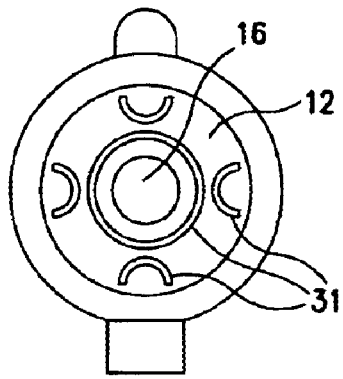
FIG. 17a    FIG. 17b
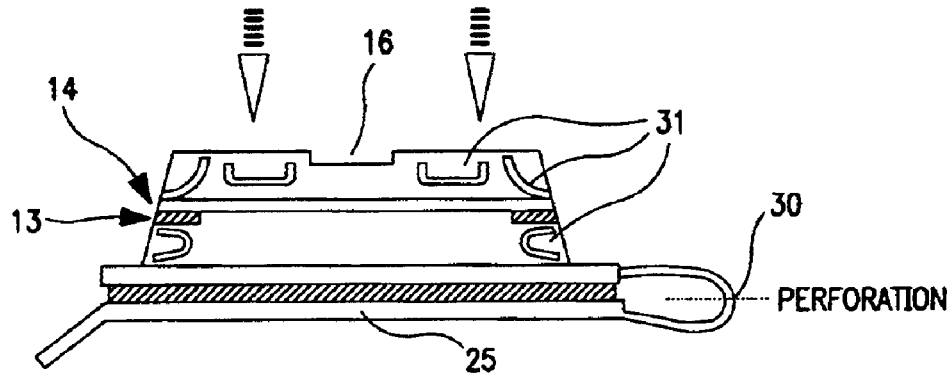
FIG. 17c
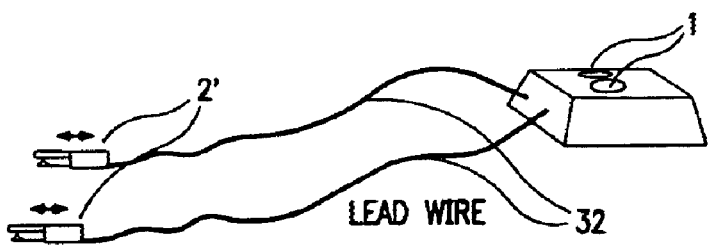
FIG. 18

IONTOPHORESIS DEVICE

TECHNICAL FIELD

The present invention relates to an iontophoresis device suitable for treatments through percutaneous and mucosal applications of drugs.

BACKGROUND ART

Recently, there have been developed a variety of dosage forms in the field of pharmaceutical preparations for external use and the development has gradually become a matter of great concern. The reason for this is as follows: The administration of a drug, which may have a local and systemic pharmacological action, through the skin or the mucous membranes has many advantages. For instance, the sustained release effect of the drug can be expected; the rate of the drug-absorption can easily be controlled and any side-effect due to the administration of an excess drug can be prevented; such administration is not greatly influenced by the metabolism due to the first-pass effect in the liver unlike the oral administration and permits the effective use of the drug; and drugs accompanied by, for instance, liver disorders can relatively safely be administered.

However, the normal skin naturally has a protective effect against external stimulations and this makes the absorption and penetration of a drug through the skin relatively difficult. For this reason, in the existing circumstances, a drug is not absorbed in an amount sufficient for ensuring a sufficient desired effect even if the drug is administered in a dosage form for external use.

Moreover, in the administration method, which makes use of absorption routes through biological membranes other than the skin, such as mouth, rectum, oral cavity and nose as well as the sublingual route, it is difficult to penetrate into or transmit through the related biological membrane depending on the kinds of drugs and therefore, there have been known a large number of drugs having low bioavailability. Accordingly, there has been desired for the development of an absorption-promoting method, which can sufficiently enhance the permeability, penetrability and absorbency of a drug against the skin and other biological membranes, can ensure a sufficient pharmacological efficacy of the drug and is substantially free of, for instance, its local and systemic toxicity and is highly useful and safe.

As such absorption-promoting methods, there have recently been known, chemically promoting methods, which make use of absorption-promoting agents; and physically promoting methods in which iontophoresis orphonophoresis is employed. Among these, the iontophoresis method has unexpectedly attracted special interest recently and has been expected as an administration method, which permits the solution of the foregoing problems. The iontophoresis method is one for the administration of a drug by applying a voltage to the skin or a mucous membrane to thus electrically induce the migration of an ionic drug and to in turn administrate the drug through the skin or a mucous membrane.

In general, an iontophoresis device has a structure comprising a combination of a layer for storing a drug therein and electrodes. An effective component in a previously designed amount and, if necessary, a variety of additives for maintaining the drug efficacy are encapsulated into the drug-storing layer for the purpose of maintaining a desired blood concentration of the effective component over a predetermined period of time. In addition, the device is provided with two electrodes, i.e., an anode and a cathode as iontophoresis electrodes and is so designed that these electrodes are arranged on or attached to the skin at a predetermined distance apart from one another and that an electric current generated by a current generator is guided to these electrodes to thus carry out treatments.

The iontophoresis device of this type is, for instance, disclosed in Japanese Un-examined Patent Publication Nos. Sho 62-268569, Hei 2-131779, Hei 3-268769; and Hei 3-45271 and TOKUHYO Nos. Hei 3-504343 and Hei 3-504813.

If a drug (such as physiologically active peptides), which suffers from a problem of the solubility in water, is used in these iontophoresis device, however, the predetermined amount of the drug may be reduced due to the partial decomposition thereof with time. Moreover, if a drug is administered in a high concentration, the drug may be diluted during storing.

If a peptide drug is percutaneously administered by the iontophoresis, it is common that the drug is not maintained in an iso-electric environment, but is kept in an acidic or basic environment. For this reason, the stability of additives, which are incorporated into the device to assist the development of the pharmacological efficacy of the biologically active substance, is greatly influenced by such acidic or basic environment and accordingly, the drug efficacy may be reduced.

Moreover, it has been recognized that in a device, which is designed in such a manner that an electrically conductive layer containing a drug in the form of a solution is directly in contact with the electrodes immediately after the electrical charging, the drug is electrolytically decomposed on the electrode surface during electrically charging the device. Accordingly, it would be doubtful whether the decomposed drug through its internal absorption adversely affects the human body.

There have been proposed a variety of methods for the solution of such a problem. For instance, Japanese Un-Examined Patent Publication No. Sho 63-102768 and U.S. Pat. No. 5,310,404 disclose a method, which comprises the steps of arranging a capsule or a porch enclosing water or an electrolyte solution above the electrode structure and breaking the capsule or porch immediately before the practical use to thus impregnate the drug-support layer therewith. This method is excellent in that the drug can be stored in a stable condition (dry state), but it is still insufficient since it takes a long period of time for uniformly permeating the moisture into the whole drug-support layer and the drug efficacy may be reduced due to the dilution of the drug.

In addition, Japanese Patent No. 2,542,792 discloses a method in which a drug-support layer and an electrode layer containing an electrolyte are separately disposed in distinct compartments, which are hinged to one another and then piling one upon another at the hinged portion to thus activate the device. This method permits the improvement in the long-term stability of a drug, but a release cover is brought into contact with the drug-support portion at the time of activating the device, the drug dissolved may accordingly be adhered to the release cover and any uniform drug content in the pharmaceutical preparation cannot be maintained at all. In addition, any means for activating the device upon application is not sufficiently devised and therefore, the method may include a lot of causes for artificial errors and cannot achieve sufficiently uniform distribution of the drug after the activation of the device. Thus, the device is not practicable.

Moreover, Japanese Un-Examined Patent Publication No. Hei 3-94771 discloses a device, which is so designed that a selective ion-permeable membrane (such as an ion-exchange membrane) is arranged such that the membrane is adjacent to the skin side of a water-support portion thereof, while a drug is dried and adhered to the side of the selective ion-permeable membrane, which is in contact with the living body, to thus prevent any dilution of the drug and to realize the administration of a trace amount of the drug to a local site in a high concentration.

Japanese Un-Examined Patent Publication No. Hei 9-201420 discloses a device for iontophoresis, in which an electrode structure layer, a solvent-support layer and a drug-support layer containing a dried physiologically active substance are put in a layer structure in this order and a water-impermeable separator later is positioned between the solvent-support layer and the drug-support layer. This device is so designed that the solvent-support layer is automatically brought into contact with the drug-support layer by pulling out the separator layer upon activation. This device is quite excellent in that the occurrence of any artificial error is prevented when assembling the device. In this device, however, the solvent-support layer and the drug-support layer are accommodated in the same package, the solubility of the drug may be reduced due to any leakage of the solvent from the solvent-support layer and accordingly, it is difficult to ensure the quality of the device. Moreover, even if it were technically possible to completely prevent the leakage of the solvent, the cost required for the development of such a technique would be very high.

As has been described above, there has not yet been developed any iontophoresis device and any method for operating the device, which can ensure the long-term stability of a drug, can easily and accurately be activated immediately before the practical use thereof and permits the elimination of any artificial error as much as possible.

Accordingly, it is an object of the present invention to provide an iontophoresis device, which can ensure the long-term stability of a drug and can easily be assembled immediately before the application.

DISCLOSURE OF THE INVENTION

The foregoing object of the present invention can be accomplished by providing an iontophoresis device having the following structure. More specifically, the inventors of this invention have conducted various studies to solve the foregoing problems and as a result, have completed the device. The device is so designed that a space is secured between a drug-support and a cover by protecting the drug-support with the cover, which is formed into, for instance, a cup-like shape to thus prevent any migration of a drug solution towards the cover. Thus, in the step for applying a predetermined amount of the drug solution to the drug-support, keeping the drug solution in the support and drying the same, the desired content of the drug in the drug-support can stably be ensured. Moreover, a hole for applying the drug solution can be formed through the cup-like cover to thus permit the practice of a series of steps, i.e., the application of the drug solution to the drug-support, the retention and drying thereof, while the cover is fitted to the drug-support and this also makes the handling of these parts upon the assemblage of the device easy and simple.

In addition, in the iontophoresis device according to the present invention, the drug-support does not directly come in contact with the release cover upon the activation of the device and therefore, any drug re-dissolved is never adhered to the release cover and any reduction of the drug content in the pharmaceutical preparation can be prevented. Moreover, upon practical use, a patient can apply the device to the body without directly putting the hand on the drug-support. Therefore, it is not necessary to fear about any adsorption of the drug on the sebum of the hand, any decomposition of the drug due to the moisture adhered to the hand, or any contamination of the drug portion with the stain, foreign substances adhered to the hand or the like. Moreover, the use of the drug-support permits the achievement of a desired administration area and the quantitative administration of the drug.

Furthermore, the iontophoresis device according to the present invention has a technical configuration described above and therefore, the drug portion and the drug-dissolving portion can separately be stored prior to the operation of the device. For this reason, if a drug whose stability to water is low (for instance, physiologically active peptides), is incorporated into the drug portion, it is not necessary to fear about the decomposition, with time, of the drug due to evaporation of water from the electrode portion provided with a built-in drug-dissolving portion. In addition, it is not needed to use any package for completely preventing any evaporation of water from the electrode and therefore, the device is also improved from the economical standpoint. Such a configuration permits the use of a stability-improving agent for the drug portion such as a drying agent, which cannot be used when the drug portion and the drug-dissolving portion are united, while taking into consideration the influence thereof on the drug-dissolving portion. Accordingly, the long-term stability of the drug can further be improved.

Moreover, the cup portion of the cover for protecting the drug-support has an additional structure for accurately put the drug portion and the drug-dissolving portion on top of each other. In this respect, the term "additional structures" means, for instance, a hole and a rod to be inserted into the hole, formed at the positions on the drug portion and the drug-dissolving portion, which coincide with one another. The drug-support portion and the drug-dissolving portion can be precisely put on top of each other by positioning of these portions while making use of the additional structure.

In addition, a hole formed on a part of the release cover of the drug-dissolving portion can be joined with the cup portion of the cover for protecting the drug-support and the drug-dissolving portion and the drug-support can be put on top of one another in a correct correlation by folding the release cover.

Further, a convex or concave frame is arranged at the periphery of the drug-dissolving portion and thus the drug-dissolving portion and the drug portion can be put on top of one another in a correct relation by incorporating the cup portion of the drug portion into the frame.

Moreover, the peripheral portion of the drug portion is formed into a concave or convex shape, while the corresponding portion on the drug-dissolving portion is likewise formed into a convex or concave shape. Thus, the drug portion and the drug-dissolving portion can be put on top of each other in a correct relation by combining these concave and convex portions.

Furthermore, the interior of the cup of the protective cover on the drug portion is formed into a shape such that the drug-support can be maintained there in and thus, the drug portion and the drug-dissolving portion can be put on top of each other in a correct relation by pressing the cup portion from the top thereof.

Moreover, the foregoing drug portion may be in the form of a drug unit, which comprises a drug-support for holding a drug and a cover arranged on at least one side of the drug-support while keeping the cover and the drug-support apart from one another. The drug unit and the drug-dissolving portion can be put on top of one another in a correct relation by forming a member for positioning at the periphery of the drug unit. In this respect, the cover of the drug unit has, for instance, a cup-like shape and the cup-like cover is provided with an opening for applying the drug.

In addition, the present invention also provide a kit for an iontophoresis device, which comprises an electrode portion provided with a drug-dissolving portion, a drug-support for holding a drug and a cover arranged on at least one side of the drug-support while keeping the cover and the drug-support apart from one another, the drug portion and the electrode portion being accommodated in separate packages. These electrode and drug portions are provided with means for positioning respectively, for putting them on top of one another.

As has been described above, the iontophoresis device according to the present invention permits the easy and correct activation of the device when practically using the same, thus permits any artificial error as low as possible and also permits the correct supply of moisture, to the drug-supply, required for re-dissolution of the drug.

BRIEF DESCRIPTION OF THE DRAWINGS

FIG. 4 is a diagram showing an embodiment of the structure of an electrode portion Ib, in which (a), (b), (c) and (d) are a view of the surface, an internal view, a view of the inner face and a cross sectional view of the electrode portion, respectively.

FIG. 8 is a diagram showing an electrode portion Ib used in Example 2, in which (a), (b), (c) and (d) are a view of the surface, an internal view, a view of the inner face and a cross sectional view of the electrode portion, respectively.

FIG. 11 is a diagram showing a drug portion Ic used in Example 3, in which (a), (b) and (c) are a top plan view of a drug-support film, a top plan view of the drug portion and a cross sectional view of the drug portion, respectively.

FIG. 12 is a diagram showing an auxiliary stand for activation used in Example 3, in which (a) and (b) are a view of the surface and a cross sectional view of the stand, respectively.

FIG. 17 is a diagram showing a drug portion Ic used in Example 5, in which (a), (b) and (c) are a top plan view of a drug-support film, a top plan view of the drug portion and a cross sectional view of the drug portion, respectively.

FIG. 18 is a diagram showing an embodiment in which a current-generating portion Ia is connected to an electrode portion Ib through a lead wire 32.

BEST MODE FOR CARRYING OUT THE INVENTION

Figure 1:
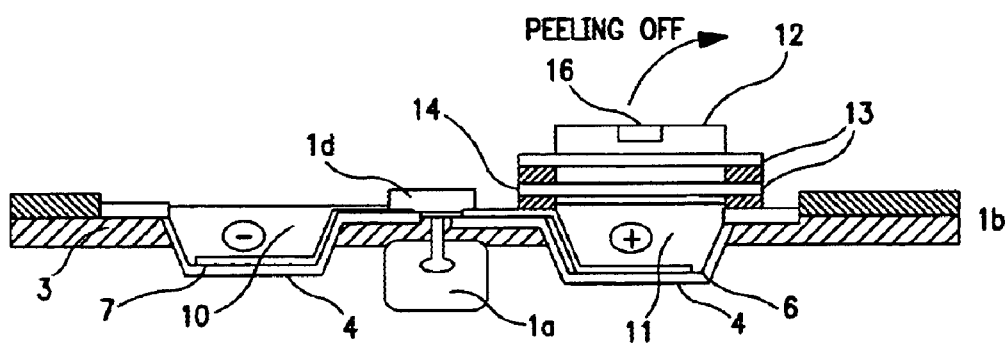
FIG. 1 is a diagram showing the cross sectional structure of an iontophoresis device according to the present invention, immediately before the practical use.

FIG. 1 is a diagram showing the cross sectional structure of an iontophoresis device according to the present invention, immediately before the practical use. In this figure, every parts are depicted separately to make, easier, the understanding of these parts which are in fact in a laminated relation or come in close contact with one another.

In this figure, a donor electrode-printed portion 6 is positioned on one side of a backing layer 4 and a reference electrode-printed portion 7 is positioned on the other side of the layer 4. An adhesive film 3 such as a medical adhesive tape is disposed on the periphery of the backing layer 4 for securing a pharmaceutical preparation to an affected part. The both electrode-printed portions 6 and 7 are connected to a current-generating portion Ia through a conductive snap connector Id. The donor electrode-printed portion 6 on the backing layer 4 is provided with a conductive layer 11 (a drug-dissolving portion) on the donor electrode side, while the reference electrode-printed portion 7 is provided with a conductive layer 10 on the reference electrode side. A drug-support film 14 as a drug-support is removably connected to the drug-dissolving portion 11. An adhesive layer 13 is formed on the drug-support 14. Thus, the drug-support film 14 is fixed to the backing layer 4 or the donor electrode-printed portion 6 through the adhesive layer 13 on the electrode portion Ib side. On the other hand, a cup-shaped protective cover 12 provided with a hole 16 for injecting a drug solution is positioned on the adhesive layer 13 on the skin side thereof.

The cup-shaped protective cover 12 is peeled off from the iontophoresis device having such a structure upon the practical use thereof and thus the drug-support film 14 is exposed. The device, which is in such a condition, is applied to the skin. Then a power supply for the current-generating portion is switched on to thus put the iontophoresis device in operation.

Embodiments of structures of each member of such an iontophoresis device will be described below in more detail.

Figure 2A:
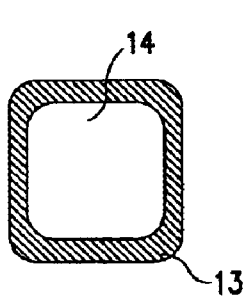
FIG. 2 is a diagram showing an embodiment of a drug portion, wherein (a), (b) and (c) are a top plan view of a drug-support film, a top plan view of the drug portion and a cross sectional view of the drug portion, respectively.
Figure 2B:
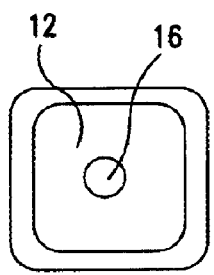
Figure 2C:
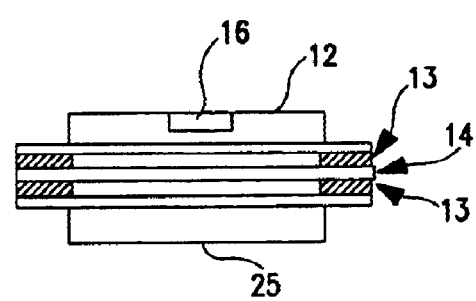
Figure 3C:
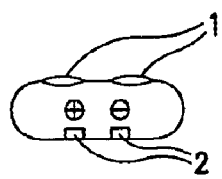
FIG. 3 is a diagram showing an embodiment of the structure of a current-generating portion Ia, in which (a) and (b) are a view of the surface and a view of the back face of the current-generating portion, and (c) and (d) are cross sectional views of the current-generating portion, respectively.
Figure 3A:
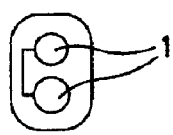
Figure 3B:
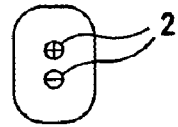
Figure 3D:
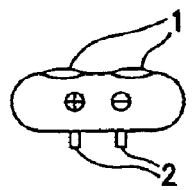

FIG. 2 is a diagram showing an embodiment of a drug portion, wherein (a), (b) and (c) are a top plan view of a drug-support film, a top plan view of the drug portion and a cross sectional view of the drug portion, respectively. The drug portion according to this embodiment is formed by sandwiching a porous drug-support film 14 in between a cover 25 on the electrode side as a protective cover and a cover 12 on the skin side. Moreover, at least the cover 12 on the skin side is formed into a cup-like shape and a hole 16 for supplying a drug solution is formed at the center of the cup. These covers 12 and 25 are formed using a film hardly adsorbing the drug such as a polyethylene terephthalate film. The drug is adhered to and supported by the drug-support film 14 by means of, for instance, spray coating or impregnation and then drying. Adhesive layers 13 are arranged on both sides of the periphery of the drug-support film 14 for ensuring the contact thereof with the electrode portion and the skin. The adhesive layer 13 is applied in a stripe pattern for ensuring air vent. In this respect, the side of the covers 12 and 25, which come in contact with the drug-support film 14 is treated with silicone in order to prevent any adsorption of a drug and to improve the releasability of the covers. Moreover, the covers may further be subjected to a treatment for preventing any diffusion of the drug in order to prevent any spreading of a drug solution even to the adhesive layer 13.

Then materials or the like for each part of the drug portion will be detailed below.

The adhesive layer 13 may be formed using adhesives as will be detailed below in connection with an adhesive film 3. This layer is desirably formed by a pattern coating technique (such as intermittent coating, stripe coating, intermittent stripe coating) to thus impart, to the layer, a structure through which the air easily passes. The width of the pattern coating is not restricted to any particular one insofar as they can ensure good balance between the adhesion and the air permeability, but the width desirably ranges from 1 mm to 20 mm.

The drug-support film 14 represented by the drug-support is not restricted to any particular one insofar as it can support a drug consisting of a physiologically active substance and permits the penetration of the drug therethrough. In addition, if the drug is a physiologically active peptide or a protein, a hydrophilic porous material may be used, which can support dried drugs and has low adsorptivity. The hydrophilic film formed from such a hydrophilic porous material includes a thin film having high wettability by water such as a hydrophilized hydrophobic (or water-repellent) polymer thin film or a hydrophilic substance-containing hydrophilic polymer film.

Examples of such hydrophilized hydrophobic polymer thin films are thin films formed from hydrophilized fluoroplastics (such as hydrophilic DURAPORE available from Millipore Ltd. and hydrophilic poly (tetrafluoroethylene) available from Toyo Roshi Co., Ltd.), thin films such as those formed from hydrophilic polyther sulfone (such as Supor available from Gelman Sciences Inc.), and hydrophilized cellulose derivatives (such as hydrophilized cellulose monoacetate and hydrophilized cellulose triacetate).

Examples of hydrophilic substance-containing hydrophilic polymer thin films include a variety of polymers obtained by adding appropriate surfactants and impregnating therewith and then drying, for instance, hydrophilized cellulose acetate films (such as Asymmetric Ultra Filter available from Sartorius Company and cellulose acetate type ones available from Toyo Roshi Co., Ltd.), hydrophilized polycarbonate films (such as Isopore Membranes available from Millipore Ltd.), hydrophilized poly (tetrafluoroethylene) films (such as Omnipore Membranes available from Millipore Ltd.), hydrophilized polysulfone films (such as HT Toughline available from Gelman Sciences Inc.) and hydrophilized nonwoven fabrics (such as films obtained by coating polyester nonwoven fabrics with cellulose acetate (for instance, coated type membranes available from Toyo Roshi Co., Ltd.)). Examples of such hydrophilic films further include nylon films (such as BIODYNE available from Nippon PALL Ltd.).

Incidentally, drugs unstable to water should desirably be included in or adhered to the drug-support in their dried condition in order to improve the stability of these drugs and to inhibit any leakage thereof. On the other hand, in case of drugs stable to water, they may be supported on the drug-support in their gel-like conditions.

In addition, as such gel-like drug-supports in other drug-supports, water-soluble polymers and hydrogel thereof are suitably used. The gel-like drug-support is prepared by kneading a gelling agent such as a water-soluble polymer and a drug solution. Moreover, the electrical conductivity of the gel-like drug-support can be enhanced by addition of an electrolyte such as sodium chloride, potassium chloride, sodium carbonate, phosphoric acid or sodium citrate; or a pH-buffering agent such as acetic acid, sodium acetate, phosphoric acid, sodium phosphate, citric acid or sodium citrate. Furthermore, the kneaded mixture is formed into a product to such an extent that it has a self shape-maintainability and then spreaded into a sheet or a film. If the kneaded mixture has an insufficient self shape-maintainability, a mesh-like support may be incorporated into the gel. The thickness of the gel layer desirably ranges from 0.1 to 2 mm and particularly preferably 0.3 to 0.8 mm. If it is extremely thin, the gel strength is considerably low, while if it is too thick, the migration of the drug is inhibited and thus, the rate of drug absorption is reduced.

The liners 12 and 25 as the protective covers may be any one insofar as they are formed from a water-impermeable material, but are desirably those capable of being processed through molding (such as thermal molding and vacuum forming). Examples of such water-impermeable materials usable herein are aluminum foils, polyester films, polypropylene films, polyethylene films and polyethylene terephthalate films as well as laminated films thereof. In addition, it is desirable to use these materials after subjecting them to an adsorption-inhibitory treatment such as a treatment with silicone or Teflon. This treatment would also facilitate the peeling off thereof from the adhesive layer 13.

Drugs usable herein may be any medicine used in any therapeutic field, which is soluble or dispersible in water and, in particular, physiologically active substances having a molecular weight ranging from $1 \times 10^2$ to $1 \times 10^6$ can widely be used. Examples of such drugs are narcotics, analgesics, anorexics, anthelmintics, drugs for asthma, anticonvulsants, antidiarrheals, antineoplastic agents, drugs for treating Parkinson's diseases, antipruritics, sympatholytic agents, xanthine derivatives, drugs for angiocardiac diseases such as calcium channel blockers, antipyretics, β-blockers, antiarrhythmic agents, hypotensive drugs, diuretics, vasodilators for blood vessels including systemic, coronary, peripheral and cerebral vessels, drugs for hemicrania, drugs for drunkness and motion sickness, antiemetics, central nervous system stimulants, drugs for cough and common cold, decogestants, diagnostics, drugs for hormonotherapy, parasympatholytic agents, parasympathomimetic agents, psychostimulants, sedatives, tranquilizers, anti-inflammatory agents, anti-arthritic agents, anti-spasmodics, antidepressants, drugs for treating psychosis, drugs for treating dizziness, anti-anxiety agents, narcotic antagonists, carcinostaticagents, hypnotics, immunosuppressors, muscle relaxants, antiviral agents, antibiotics, anorexics, antiemetics, anti-cholinergicagents, antihistamic agents, contraceptives, antithrombotic agents, bone-absorption suppressors and osteogenesis-promoting agents. However, the present invention is not restricted to these specific drugs. These drugs may be used alone or in any combination.

Specific examples of these drugs include steroids such as estradiol, progesterone, norgestrel, levonorgestrel, norethindrone, medroxy-progesterone acetate, testosterone and esters thereof; nitro group-containing compounds and derivatives thereof such as nitroglycerin and isosorbide dinitrates, nicotine, chlorpheniramine, terfenadine, triprolidine and hydrocortisone; anti-inflammatory drugs such as piroxicam, ketoprofen, mucopolysaccharidases such as thiomucase, buprenorphine, fentanyl, naloxone, codeine, lidocaine, dihydroergotamine, pizotyline, salbutamol and terbutaline; prostaglandins such as misoprostol, enprostil, omeprazole and imipramine; benzamides such as metoclopramine, scopolamine and clonidine; dihydropyridines such as nifedipine, verapamil, ephedrine, pindolol, metoprolol, spironolactone, nicardipine HCl and calcitriol; thiazides such as hydro-chlorothiazide and flunarizine; sydnone imines such as molsidomine; sulfated polysaccharides such as heparin fractions and proteins; and peptides such as insulin and homologues thereof; calcitonins and homologues such as elcatonin, protamin and glucagone; globulins, angiotensin I, angiotensin II, angiotensin III, lypressin, vasopressin, somatostatin and homologues thereof; growth hormones and oxytocin; as well as, if necessary, pharmaceutically acceptable salts thereof with acids or bases.

Preferred are, for instance, narcotics, hormones, proteins, analgesics, or other low molecular weight cations. More preferably, examples of drugs include peptides or polypeptides such as insulin, calcitonin, calcitonin-related geneticpeptides, vasopressin, desmopressin, protirelin (TRH), adrenocorticotropic hormones (ACTH), luteinizing hormone-release hormones (LH-RH),growth hormone-release hormone (GRH), nerve growth factors (NGF) and other release factors, angiotensins, parathyroid hormone (PTH), luteinizing hormone (LH), prolactin, serumal gonadotropin, hypophyseal hormones (such as HGH, HMG, HCG), growth hormones, somatostatin, somatomedin, glucagon, oxytocin, gastrin, secretin, endorphin, enkephalin, endothelin, cholecystokinin, neurotensin, interferon, interleukin, transferrin, erythropoietin, superoxide dismutase (SOD), filgrastim (G-CSF), vasoactive-intestinal-polypeptides (VIP), muramyl dipeptides, corticotropin, urogastrone and atrial sodium uragogue peptides (h-ANP). However, the present invention is not restricted to these specific drugs. Among these, particularly preferred are peptide hormones.

It is also possible to optionally use adsorption-inhibitory agents such as benzalkonium chloride, BSA (bovine serum albumin) and monolauric acid.

In the present invention, at least one of the foregoing drugs and salts thereof may be supported on the drug-support film. In addition, the amount of the drug is determined depending on a particular drug in such a manner that upon administration thereof to a patient, a predetermined effective blood concentration is maintained over an effective period of time and the size of the iontophoresis device as well as the area of the drug-delivery surface thereof are determined in proportion thereto.

FIG. 3 is a diagram showing an embodiment of the structure of a current-generating portion Ia, in which (a) and (b) are a view of the surface and a view of the back face of the current-generating portion, and (c) and (d) are cross sectional views of the current-generating portion, respectively. The current-generating portion Ia is a plastic molded body having therein a built-in current control circuit. A current control switch 1 is arranged on the top of the current-generating portion, while a female or male electrode terminal 2 (one each of the terminal on the sides of the anode and cathode) is arranged below the current-generating portion. This current-generating portion Ia is preferably designed such that no physical burden due to the size and weight thereof is given to a patient.

More specifically, the current-generating portion is constituted by a self-oscillator circuit provided with a built-in small-sized cell, an appropriate high voltage-generating circuit connected to the oscillator circuit and a control circuit for operating and controlling these circuits. It is also possible to incorporate a BOLUS button for temporarily increasing the rate of drug-injection into the current-generating portion. This is quite useful function when an analgesic is administered to a patient and the patient desires for a temporary increase in the dose thereof in proportion to the degree of his pains.

Moreover, the control circuit is, for instance, designed in such a manner that the circuit permits the manual on/off switching in order to allow the on-demand medication regime and the on/off switching at a period adapted for the biological circadian rhythm and the pattern at intervals of 24 hours. In addition, the control circuit may be equipped with a built-in microprocessor and therefore, the circuit permits the modification of the level and pulse of the current to be applied over a predetermined time and the wave form of sinusoidal waves. Moreover, the control circuit may comprise a biosensor or a certain kind of feedback system for monitoring the biosignals of a patient, evaluating the treating method and adjusting the amount of the drug to be administered to the patient in response to the results of the evaluation. It is also possible to incorporate, into the control circuit, at least one program established, in advance, by the maker of the drug, a physician or a patient.

FIG. 4 is a diagram showing an embodiment of the structure of an electrode portion Ib, in which (a), (b), (c) and (d) are a view of the surface, an internal view, a view of the inner face and a cross sectional view of the electrode portion, respectively. The electrode portion has a backing layer 4 consisting of a film of a polyolefin such as polyester or polypropylene or a molded body of such a film laminated with an aluminum layer. A donor electrode-printed portion 6 and a reference electrode-printed portion 7 are arranged on the molded backing layer 4 and they are formed by printing silver (on the anode side) and silver chloride (on the cathode side). Moreover, two insertion openings 5 (one each of the opening on the sides of the anode and cathode) for conductive snap connectors are positioned on the printed electrode portions 6 and 7 at the center of the backing layer. Furthermore, the electrode portion is provided with a frame 27 for ensuring a space for accommodating the cup-like molded protective cover.

A conductive layer 10 on the reference electrode side and a conductive layer (drug-dissolving portion) 11 on the donor electrode side are formed on the electrode portion in such a manner that they are adjacent to the printed electrode portions 6 and 7 and the material used for forming these layers is a water-retentive material such as a nonwoven fabric or a hydrophilic polymer, which comprises an electrolyte. In this respect, the conductive layer 11 on the donor electrode side (in this embodiment, the layer on the anode side) also serves as a moisture supply source for the drug accommodated in the drug portion upon activation.

Moreover, the conductive layers are packaged with a water-impermeable cover material 9 through easily peeled heat seal in order to prevent any moisture evaporation during storage. Further an adhesive film 3 such as a medical adhesive tape is applied onto the periphery of the backing layer 4 for the purpose of fixing the pharmaceutical preparation to an affected site and a liner is fitted to the adhesive film during storage. Moreover, a liner 8 for the adhesive film is fitted during storage.

Incidentally, these electrode portions 6 and 7 may have any electrode structure inasmuch as they have any conventionally known electrode structure. For instance, usable herein are materials such as platinum black, titanium, carbon, aluminum, iron, lead, carbon-containing conductive rubber, conductive resins, platinum electrode, silver electrode and silver chloride electrode, with platinum electrode, silver electrode, silver chloride electrode or the like being desirably used herein.

In addition, the cover material 9 is not restricted to any particular one insofar as it is formed from a water-impermeable material. For instance, the cover material is formed from a film laminated with an aluminum layer. If a highly sealed condition by heat sealing is required, the cover material is laminated with a plurality of films such as those described above in connection with the liner or it is coated with another polymer resin. This makes the peeling off of the cover material easy. For instance, there can be used an easily peelable laminate film. It is desirable that the laminate film have a peel strength at 180 degrees of 2000 g or less.

A pressure-sensitive adhesive is used as a material for the adhesive film 3. Any pressure-sensitive adhesive may be used herein insofar as they can maintain the iontophoresis device on the surface of the skin or mucous membrane of a patient, while the device is brought into close contact therewith, they have an adhesive force sufficient for ensuring good adhesion of the drug portion to the drug-dissolving portion and they are physiologically acceptable for the skin. Specific examples thereof are acrylic adhesives comprising homopolymers or copolymers of alkyl acrylates whose alkyl moiety has 4 to 18 carbon atoms, such as acrylic acid, methyl acrylate, ethyl acrylate, 2-ethylhexyl acrylate, isooctyl acrylate, decyl acrylate, lauryl acrylate and stearyl acrylate; methacrylic adhesives comprising homopolymers or copolymers of alkyl methacrylates whose alkyl moiety has 4 to 18 carbon atoms, such as methyl methacrylate, ethyl methacrylate, butyl methacrylate, 2-ethylhexyl methacrylate, isooctyl methacrylate, decyl methacrylate, lauryl methacrylate and stearyl methacrylate; silicone type adhesives such as those comprising poly-organosiloxane and polydimethyl-siloxane; and rubber type adhesives such as those comprising natural rubber, poly-isobutylene, polyvinyl ether, polyurethane, polyisoprene, poly-butadiene, styrene-butadiene copolymer, styrene-isoprene copolymer and styrene-isoprene-styrene block copolymer. Moreover, the adhesive material may, if necessary, comprise a tackifier and a softening agent.

A material for the backing layer 4 herein used may be an effective component-impermeable material. Examples thereof are films, sheets and foams of synthetic resins such as polyethylene, polypropylene, polyethylene terephthalate, polyvinyl chloride, polyvinylidene chloride, plasticized vinyl acetate copolymer, plasticized vinylacetate-vinyl chloride copolymer, polyamide, cellophane, cellulose acetate, ethyl cellulose, polyester, polycarbonate, polystyrene, polyurethane, polybutadiene, polyimide, poly-acrylonitrile, polyisoprene, polystyrene derivatives, ethylene-vinyl acetate copolymer, ethylene-polyvinyl alcohol copolymer, fluoroplastics, acrylic resins, epoxy resins, which maybe used alone or in the form of a laminate of at least two of them.

In addition, the films, sheets, foams or the like of these synthetic resins may be laminated with metal foils such as aluminum and tin foils; nonwoven fabrics and synthetic paper or may be covered with deposited aluminum layers and ceramic coatings. Moreover, if closed package by, for instance, heat sealing is required, they may be laminated with a heat-sealable material.

The electrode portion may be deposited on the backing layer as a container material by, for instance, a method comprising the steps of mixing the foregoing electrode material with, for instance, a print ink for electric distributing wires, applying the print ink to a material for the backing layer and then drying the same; a method comprising the step of printing and fixing the foregoing electrode material to the backing layer; a method comprising the step of vapor-depositing the foregoing electrode material to the backing layer; and a method comprising the step of applying the foregoing electrode material to the backing layer through a photoetching technique. In addition, an insulating layer may additionally be applied onto a part of the printed electrode layer, which may come in contact with the skin of a patient.

The conductive layer may simply comprise water or may comprise at least one member selected from the group consisting of soft porous materials such as ion-exchangeable polymers, foaming materials and sponge and water-absorptive polymers. Moreover, the conductive layer may comprise an electrolyte such as sodium chloride, potassium chloride, sodium carbonate, phosphoric acid or sodium citrate; or a pH-buffering agent such as acetic acid, sodium acetate, phosphoric acid, sodium phosphate, citric acid or sodium citrate, for the improvement of the electric conductivity thereof.

Specific examples of the preferably used conductive layer in general include nonwoven fabric, paper, gauze, absorbent wadding, polyethylene or polypropylene having open cells, polyvinyl acetate, porous films and foams of, for instance, polyolefin foams, polyamide foams and polyurethane; natural polysaccharides such as karaya gum, tragacanth gum, xanthane gum, starches, gum arabic, locust bean gum and gellan gum; gelatin, pectin, agar, sodium alginate or polyvinyl alcohol and partially saponified products thereof; polyvinyl formal, polyvinyl methyl ether and copolymers thereof; polyvinyl pyrrolidone and copolymers thereof; hydrophilic or water-soluble cellulose derivatives such as sodium carboxymethyl cellulose, methyl cellulose, hydroxyethyl cellulose, hydroxy cellulose, hydroxypropyl methyl cellulose, hydroxypropyl cellulose and cellulose acetate phthalate; carboxyvinyl polymer, polyacrylamide and polyacrylamide derivatives, casein, albumin, chitin, chitosan, sodium polyacrylate, poly-HEMA, poly-HEMA derivatives, as well as crosslinked products thereof, water-soluble polymers optionally plasticized with, for instance, ethylene glycol or glycerin and hydrogels thereof, which are used under non-aqueous conditions. However, the present invention is not restricted to these specific ones. In addition, the foregoing materials may be used in combination of at least two of them. Moreover, it is also possible to use, if necessary, an adsorption-inhibitory agent such as benzalkonium chloride and BSA (bovine serum albumin).

Furthermore, the conductive layer may also comprise an ion-exchangeable polymer for the removal of ions competitive with a desired drug. Such an ion-exchangeable polymer usable herein is appropriately selected from anion-exchange polymer, cation-exchange polymer or ampholyticion-exchangeable polymer, depending on the ionic properties of each particular drug. In addition, the ion-exchangeable polymer may be incorporated into the conductive layer by, for instance, a method comprising the step of dispersing fine powder of an ion-exchangeable polymer in the foregoing polymer to thus form the mixture into a gel-like form or a method, which makes use of a product of such an ion-exchangeable polymer previously formed into a film, but the present invention is not restricted to these specific methods at all.

The capacity of the conductive layer on the donor electrode side (drug-dissolving portion) is not particularly restricted to a specific range, but depends on, for instance, the size of the electrode portion and the optimum amount of water required for dissolving a drug accommodated in the drug portion, or the water content of the absorptive member of the drug-dissolving portion. In this respect, however, if the amount of water is too large, it may cause leakage of the drug-dissolving liquid, while if it is too small, the drug present in the drug portion cannot completely be dissolved and the drug efficacy is correspondingly reduced. Therefore, the amount of water is desirably on the order of the maximum water absorption of the drug portion. If a hydrogel is used in the drug-dissolving portion, syneresis thereof particularly preferably ranges from 10 to 100 mg/cm$^2$. Moreover, the hydrogel should have such gel strength that the gel is never broken during the activation of the device and during the application thereof to the skin and therefore, the hydrogel desirably has a gel strength ranging from 400 to 1500 mg/cm$^2$.

The amount of water required for dissolving a drug present in the drug-support is, in advance, controlled in the drug-dissolving portion. Thus, a precise amount of water can certainly and rapidly be supplied to the drug-support at any time upon practical use and this makes the therapeutic effect accurate. Moreover, this can also simplify the treating operations and reduce the treating time.

Figure 5A:
FIG. 5 is a diagram showing an embodiment of the structure of a conductive snap connector Id, in which (a) is a view of the surface, and (b) and (c) are cross sectional views of the connector, respectively.
Figure 5B:
Figure 5C:

FIG. 5 is a diagram showing an embodiment of the structure of a conductive snap connector Id, in which (a) is a view of the surface, and (b) and (c) are cross sectional views of the connector, respectively. This connector is provided with two electrode terminals 18 (male and female) on an electrode terminal fixing table 17 such that they can be connected to the electrode terminals 2 (female and male) of the current-generating portion Ia.

The current-generating portion Ia is connected to the electrode portion Ib such that the latter is sandwiched in between the electrode terminal on the side of the current-generating portion Ia and that on the side of the conductive snap connector Id. The electrode terminal on the conductive snap connector side comes in contact with the printed electrode portion (either of the anode and cathode) of the electrode portion due to the connection. Accordingly, the current-generating portion and the electrode portion can electrically be charged and the electrical connection can thus be established.

In respect of the modes of the connection of the current-generating portion to the electrode portion, the device may be operated in a cordless mode or a remote control mode using a cord. In case of the former, a small-sized current-generating portion is directly connected to the electrode portion when it is intended to carry out an easy and quick treatment. Besides, in case of the latter, the current-generating portion is connected to the electrode portion through an exclusive connecting flex when it is intended to carry out a treatment while operating the current-generating portion at hand. In this connection, connection means are fitted to the both sides of the connecting flex for connecting the current-generating portion to the conductive snap connector. In this embodiment, electrode terminals (for both anode and cathode) are incorporated into a plastic molded body so that it serves to connect the terminals, to each other, on the sides of the current-generating portion and the conductive snap connector. In this respect, the connection means is not restricted to an electrode terminal and the shape and the connection mode thereof may arbitrarily be changed. Preferably, the connection means on the conductive snap connector side has such a structure that the drug portion and the electrode portion are in line with each other and they can firmly maintain a desired arrangement.

Then, the method for laminating or assembling the iontophoresis device, which makes use of the foregoing component parts, according to the following Examples 1 to 5, will be hereunder described.

EXAMPLE 1

Figure 6:
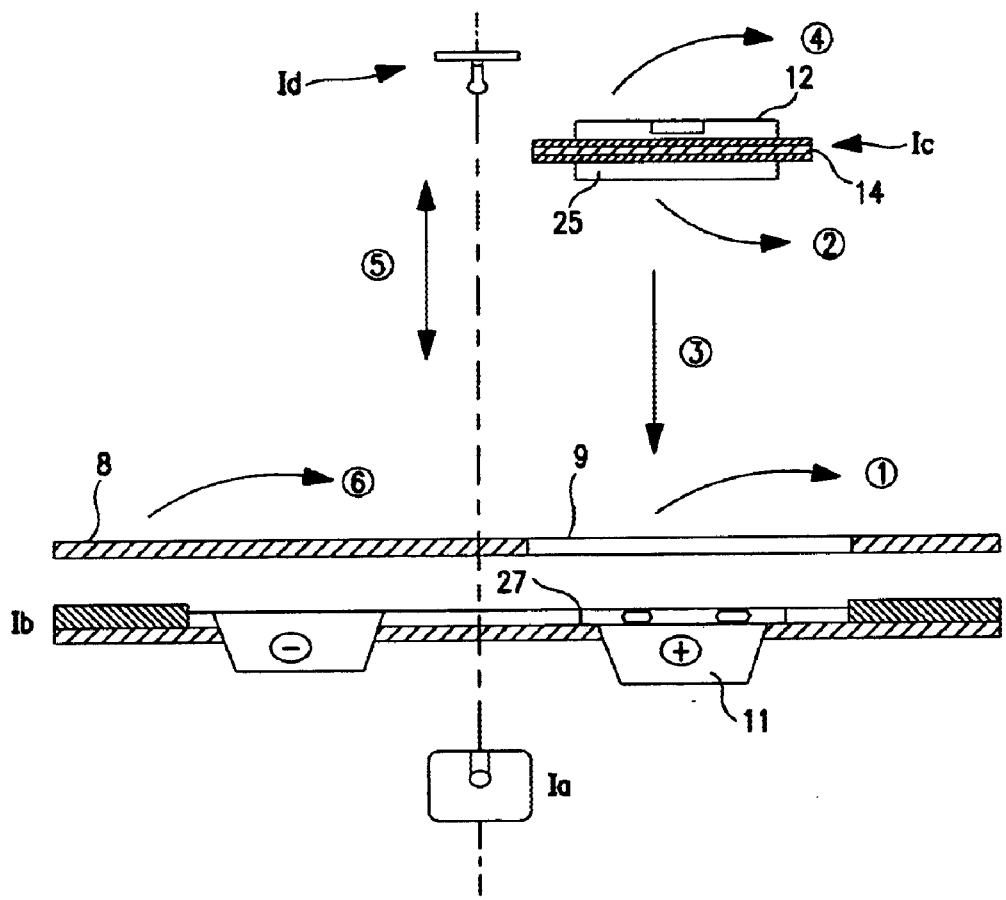
FIG. 6 is a diagram for explaining a method for activating the iontophoresis device according to Example 1.

FIG. 6 is a diagram for explaining a method for activating the iontophoresis device of Example 1. The procedures for the activation are as follows:

Operational Procedure ①: A cover material 9 of an electrode portion Ib is peeled off to thus expose a drug-dissolving portion 11.

Operational Procedure ②: A cover 25 on the electrode side among protective covers sandwiching a drug-support film therebetween is peeled off.

Operational Procedure ③: After the release of the cover 25 on the electrode side, the drug portion Ic and the drug-dissolving portion 11 are brought into contact with one another without any aberration of their positions, in such a manner that a cup-shaped protective cover coincides with a frame 27 for ensuring a space for accommodating the cup-like protective cover to thus integrally combine the drug-support film 14 with the drug-dissolving portion 11.

Operational Procedure ④: After the assemblage, a cover 12 on the skin side is released.

Operational Procedure ⑤: Separate and individual three portions, i.e., a current-generating portion Ia, the drug portion Ic and the electrode portion Ib are brought into contact with each other using a snap connector Id.

Operational Procedure ⑥: A liner 8 for an adhesive film of the drug portion Ib is released. Thus, the device can be applied to the skin without any pretreatment and the treatment of a patient can thus be initiated.

In this respect, the operational procedures for the activation of the device is not restricted to that described above and can be modified depending on the modes of application thereof to a patient and depending on various circumstances.

As has been described above, in the iontophoresis device of Example 1, the cover 25 on the electrode side among the protective covers for the drug-support film is first released and then the cup-shaped protective cover 12 is put in the frame 27 for ensuring the space for accommodating the cup-shaped protective cover to thus permit the positioning of the drug portion Ic and the drug-dissolving portion 11. Therefore, the iontophoresis device of Example 1 can easily and precisely be activated upon application of the device. In addition, the device also permits the elimination of any artificial error as low as possible and precise supply, to the drug layer, of moisture required for re-dissolving the drug.

EXAMPLE 2

The iontophoresis device according to Example 2 has a structure almost identical to that of the iontophoresis device of Example 1, except that the positioning of the drug portion Ic and the drug-dissolving portion 11 and the activation of the drug are performed using a positioning cover-molded and fabricated portion 28, which is realized by molding and shaping the periphery of the protective cover 12 for the drug-support film.

Figure 7A:
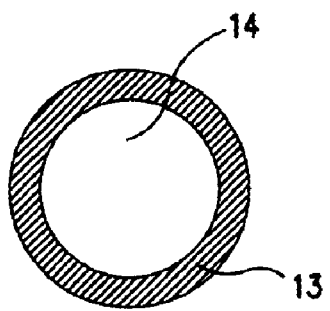
FIG. 7 is a diagram showing a drug portion Ic used in Example 2, in which (a), (b) and (c) are a top plan view of a drug-support film, a top plan view of the drug portion and a cross sectional view of the drug portion, respectively.
Figure 7B:
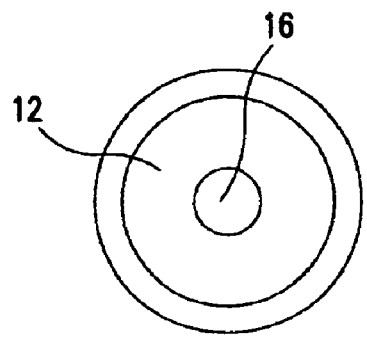
Figure 7C:
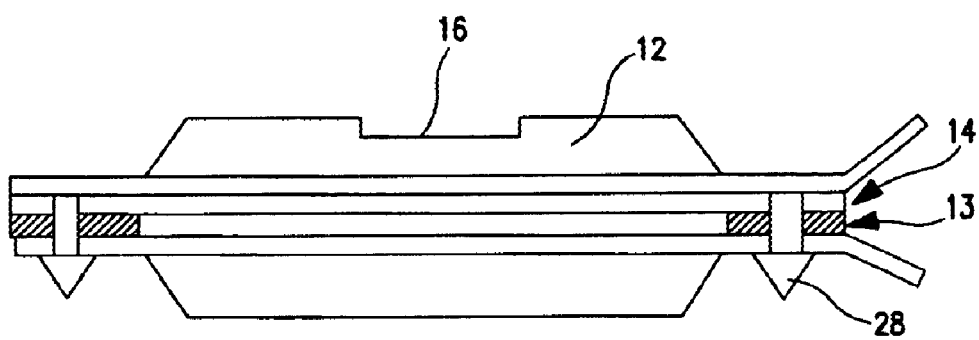

FIG. 7 is a diagram for showing the drug portion Ic used in Example 2, in which (a) is a top plan view of the drug-support film, (b) is a top plan view of the drug portion and (c) is a cross sectional view of the drug portion, respectively. As will be seen from this figure, the drug portion is provided with the positioning cover-molded and fabricated portion 28.

FIG. 8 is a diagram showing the electrode portion Ib used in Example 2, in which (a), (b), (c) and (d) are a view of the surface, a view of the interior, a view of the inner face and a cross sectional view of the electrode portion, respectively. As will be seen from this figure, the electrode portion is provided with a hole 29 or an insertion hole corresponding to or for receiving the positioning cover-molded and fabricated portion 28 of the drug portion as shown in FIG. 7.

In this Example 2, the current-generating portion Ia and the snap connector Id have structures identical to those of the device according to Example 1 as shown in FIGS. 3 and 5, respectively.

Figure 9:
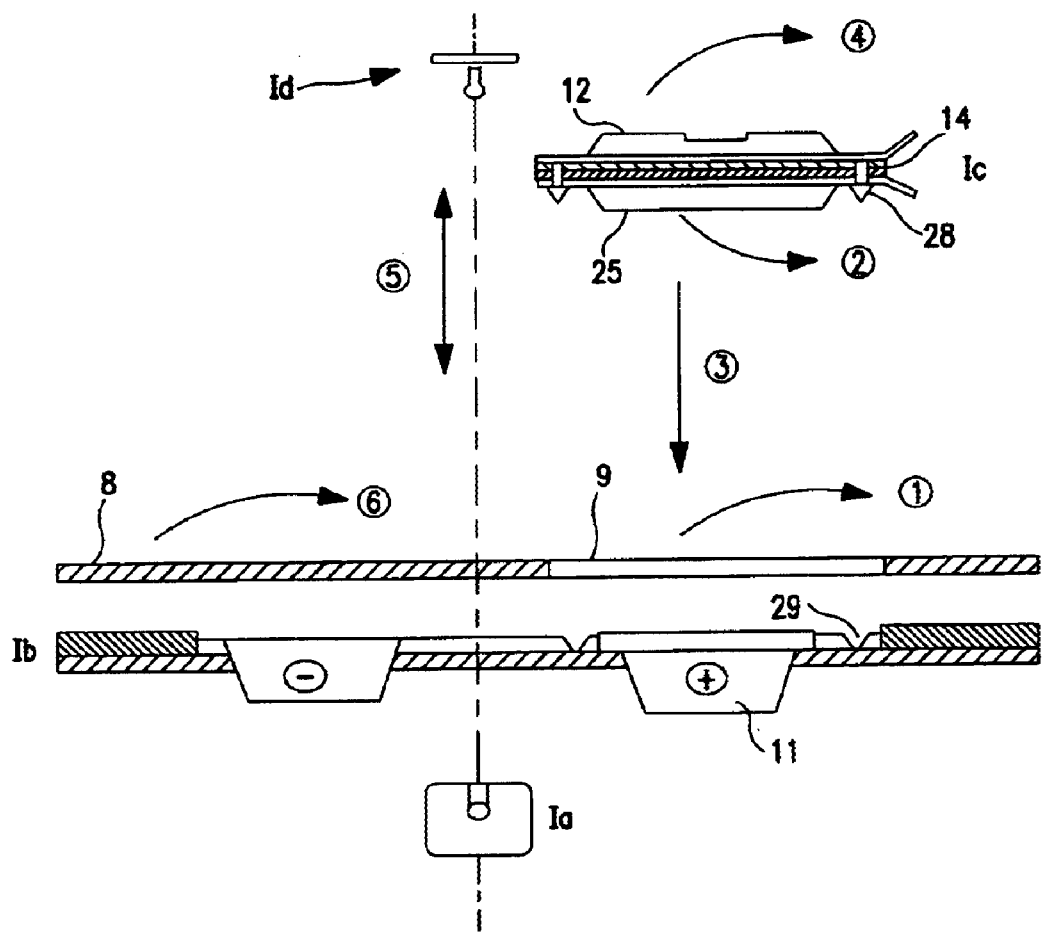
FIG. 9 is a diagram for explaining a method for activating the iontophoresis device according to Example 2.
Figure 10A:
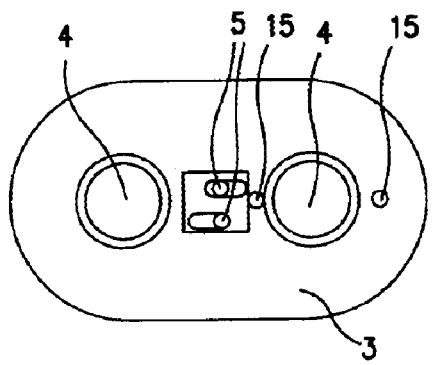
FIG. 10 is a diagram showing an electrode portion Ib used in Example 3, in which (a), (b), (c) and (d) are a view of the surface, an internal view, a view of the inner face and a cross sectional view of the electrode portion, respectively.
Figure 10B:
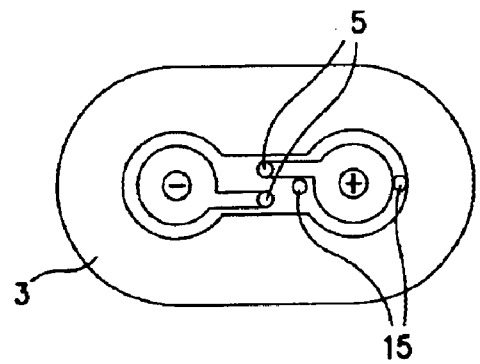
Figure 10C:
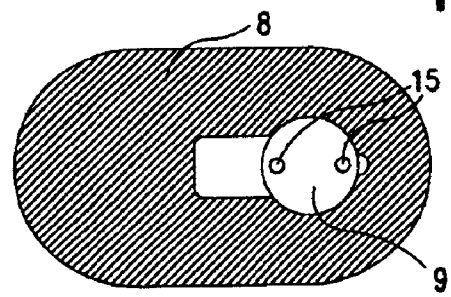
Figure 10D:
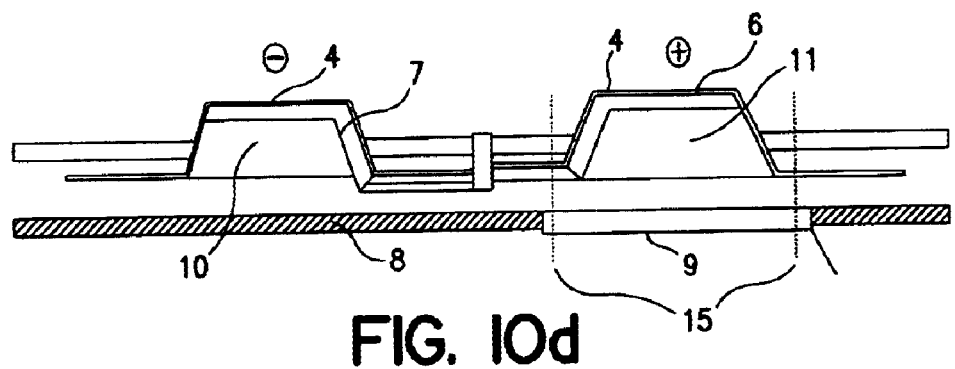

FIG. 9 is a diagram for explaining the method for activating the iontophoresis device according to Example 2. The activation of the device can be performed by the following procedures:

Operational Procedure ①: A cover material 9 of an electrode portion Ib is peeled off to thus expose a drug-dissolving portion 11.

Operational Procedure ②: A cover 25 on the electrode side among protective covers sandwiching a drug-support film therebetween is peeled off.

Operational Procedure ③: After the release of the cover 25 on the electrode side, the drug portion Ic and the drug-dissolving portion 11 are brought into contact with one another without any aberration of their positions, in such a manner that the positioning cover-molded and fabricated portion 28 of the molded cover coincides with the hole 29 for the positioning cover-molded and fabricated portion to thus integrally combine the drug-support film 14 with the drug-dissolving portion 11.

Operational Procedure ④: After the assemblage, a cover 12 on the skin side is released.

Operational Procedure ⑤: Separate and individual three portions, i.e., a current-generating portion Ia, the drug portion Ic and the electrode portion Ib are brought into contact with each other using a snap connector Id.

Operational Procedure ⑥: A liner 8 for an adhesive film of the drug portion Ic is released. Thus, the device can be applied to the skin without any pretreatment and the treatment of a patient can thus be initiated.

In this respect, the operational procedures for the activation of the device is not restricted to that described above and can be modified depending on the modes of application thereof to a patient and depending on various circumstances.

As has been described above, in the iontophoresis device of Example 2, the molded and fabricated portion 28 obtained by molding and fabricating the periphery of the cup-shaped protective cover 12 is inserted into the hole 29 or the insertion hole, which is formed on the corresponding portion at the periphery of the drug-dissolving portion 11 to thus permit the positioning of the drug portion Ic and the drug-dissolving portion 11. Therefore, the iontophoresis device of Example 2 can easily and precisely be activated upon application of the device. In addition, the device also permits the elimination of any artificial error as low as possible and precise supply, to the drug layer, of moisture required for re-dissolving the drug.

EXAMPLE 3

The iontophoresis device of Example 3 has a structure almost identical to those of the iontophoresis devices of Examples 1 and 2 except that the positioning of the drug portion Ic and the drug-dissolving portion 11 and the activation of the drug are carried out using an auxiliary stand Ie for the activation.

FIG. 10 is a diagram showing an electrode portion Ib used in Example 3, in which (a), (b), (c) and (d) are a view of the surface, a view of the interior, a view of the inner face and a cross sectional view of the electrode portion. As will be seen from this figure, the electrode portion is provided with a hole 15 for inserting a positioning rod.

FIG. 11 is a diagram showing a drug portion Ic used in Example 3, in which (a), (b) and (c) are a top plan view of a drug-support film, a top plan view of the drug portion and a cross sectional view of the drug portion, respectively. As will be clear from FIG. 11, the drug portion is provided with a hole 15' for inserting a positioning rod.

FIG. 12 is a diagram showing the auxiliary stand Ie for activation used in Example 3, wherein (a) and (b) are a view of the surface and a cross sectional view of the auxiliary stand. The auxiliary stand Ie for activation is so designed that it has a space 20 for accommodating the electrode portion, whose shape coincides with that of the backing layer 4 of the electrode portion and that it also has two positioning rods 19 used in the assemblage of the device. The material for the auxiliary stand is not restricted to any specific one insofar as it can be molded and fabricated and examples thereof include paper, metals, wood and plastic films (polypropylene, Teflon and polyvinyl chloride), with plastic films having a thickness of not less than 3 mm and high molded shape-maintaining properties being preferred.

This auxiliary stand for activation is so designed that a patient can easily carry out the lamination or assemblage of the device. The iontophoresis device according to this Example is provided with the space 20 for accommodating the electrode portion, whose shape coincides with that of the backing layer 4 of the electrode portion and the space permits precise arrangement of the electrode portion on the auxiliary stand for activation. Moreover, the space 20 for accommodating the electrode portion is also useful in that it can prevent any breakage or damage of the electrode portion upon the lamination of the device. In addition, the positioning rods 19 are provided for making the positioning of the electrodes and the drug-support film during laminating or assembling the device easy and simple and are effective for inhibiting the occurrence of any artificial error.

Incidentally, the structures of the current-generating portion Ia and the snap connector Id used in Example 3 are the same as those used in Example 1 and shown in FIGS. 3 and 5.

Figure 13:
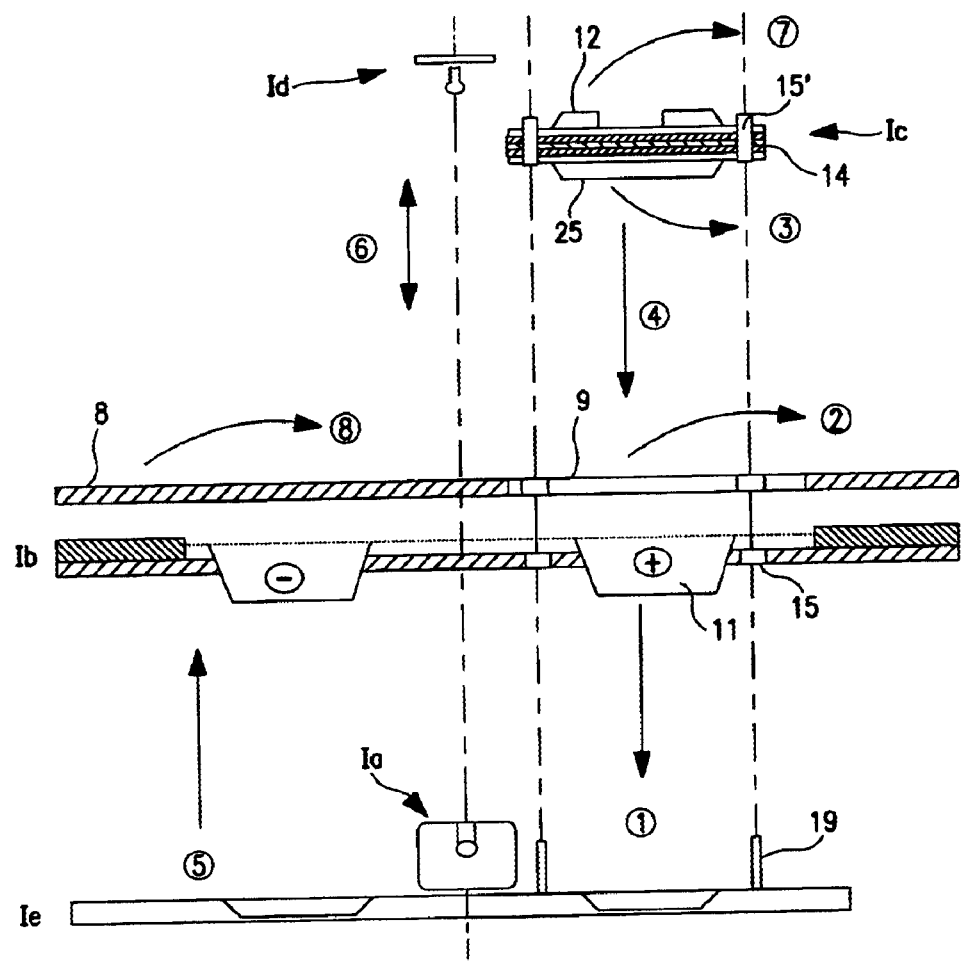
FIG. 13 is a diagram for explaining a method for activating the iontophoresis device according to Example 3.

FIG. 13 is a diagram for explaining the method for activating the iontophoresis device of Example 3. The procedures therefor are as follows:

Operational Procedure (1): The electrode portion Ib is fitted to the auxiliary stand Ie by coinciding the positioning rod 19 of the auxiliary stand Ie for activation with the insertion hole 15 of the electrode portion Ib.

Operational Procedure (2): The cover material 9 of the electrode portion Ib is released to thus expose the drug-dissolving portion 11.

Operational Procedure (3): The cover 25 on the electrode side, which protects the drug-support film 14 of the drug portion Ic is removed.

Operational Procedure (4): The positioning rod 19 is inserted into the insertion hole 15' to bring the drug portion Ic into contact with the drug-dissolving portion 11 without any aberration of their positions and to thus integrally combine the drug-support film 14 of the drug portion with the drug-dissolving portion 11.

Operational Procedure (5): A pharmaceutical preparation comprising the electrode portion Ib and the drug portion Ic is removed from the auxiliary stand Ie for activation.

Operational Procedure (6): Separate and independent three portions, i.e., the current-generating portion Ia, the drug portion Ic and the electrode portion Ib are brought into contact with one another using the snap connector Id.

Operational Procedures (7): The cup-shaped molded protective cover 12 of the drug portion Ic and the liner 8 for the adhesive film are released. Thus, the device can be applied to the skin without any pre-treatment and the treatment of a patient can be initiated.

In this respect, the operational procedures for the activation of the device is not restricted to that described above and can be modified depending on the modes of application thereof to a patient and depending on various circumstances.

As has been described above, in the iontophoresis device of Example 3, the insertion of the positioning rod 19 of the auxiliary stand Ie for activation into the insertion hole 15' formed at the periphery of the cup-shaped protective cover 12 permits the positioning of the drug portion Ic and the drug-dissolving portion 11. Therefore, the iontophoresis device of Example 3 can easily and precisely be activated upon application to the skin or mucous membrane. In addition, the device also permits the elimination of any artificial error as low as possible and precise supply, to the drug layer, of moisture required for re-dissolving the drug.

Moreover, the use of the positioning rod 19 of the auxiliary stand Ie for activation makes the handling of the means for positioning the drug portion Ic and the drug-dissolving portion 11 easy. Accordingly, this can eliminate any operational error of a patient upon activation.

EXAMPLE 4

The iontophoresis device of Example 4 has a structure approximately identical to those of the iontophoresis devices of Examples 1, 2 and 3 except that a hole 21 for capable of inserting or receiving the cup portion of the cup-shaped protective cover 12 of the drug portion is positioned at a position on an extended liner 8 for the adhesive film and that the cover on the electrode side among the protective covers of the drug portion has a flat structure.

Figure 14A:
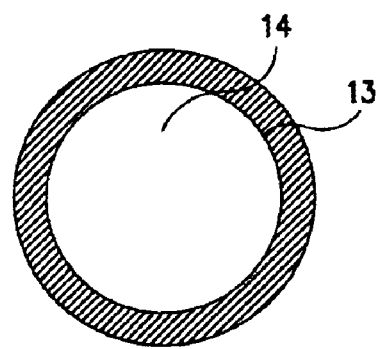
FIG. 14 is a diagram showing a drug portion Ic used in Example 4, in which (a), (b) and (c) are a top plan view of a drug-support film, a top plan view of the drug portion and a cross sectional view of the drug portion, respectively.
Figure 14B:
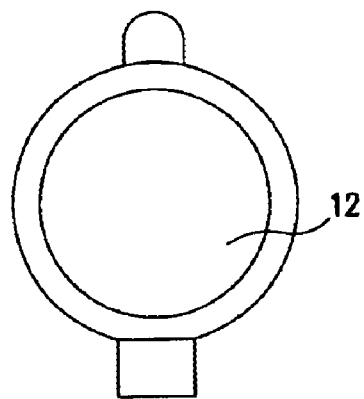
Figure 14C:
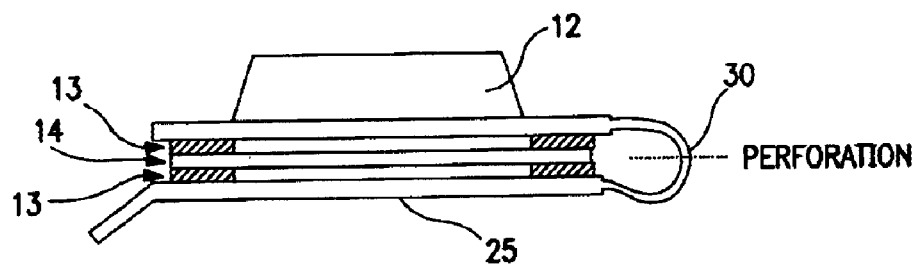
Figure 15A:
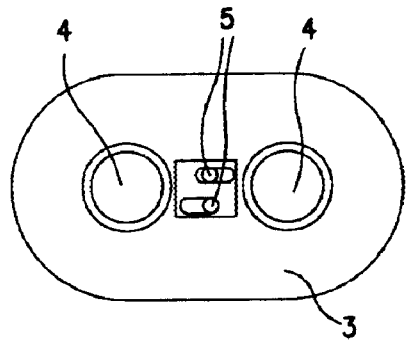
FIG. 15 is a diagram showing an electrode portion Ib used in Example 4, in which (a), (b), (c) and (d) are a view of the surface, an internal view, a view of the inner face and a cross sectional view of the electrode portion, respectively.
Figure 15B:
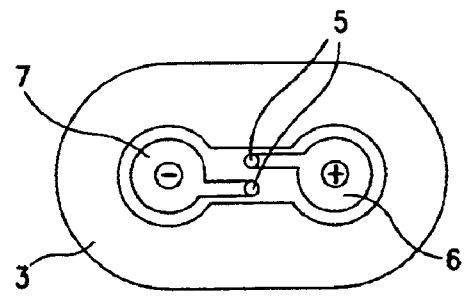
Figure 15C:
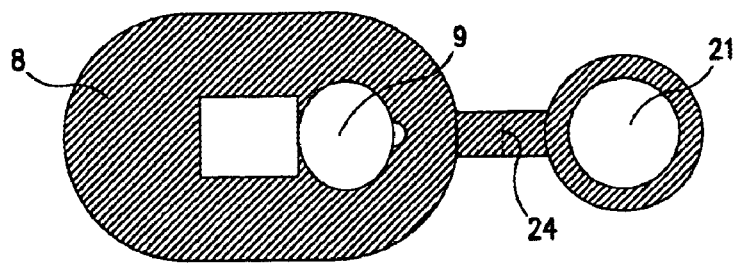
Figure 15D:
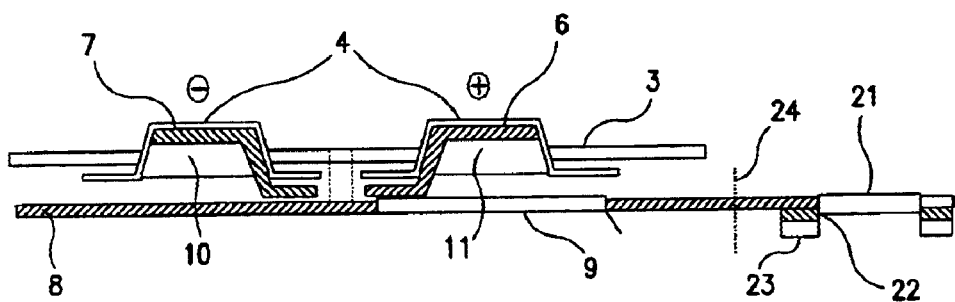

FIG. 14 is a diagram showing the drug portion Ic used in Example 4, wherein (a), (b) and (c) are a top plan view of the drug-support film, a top plan view of the drug portion and a cross sectional view of the drug portion, respectively. As will be seen from this figure, the drug portion is provided with a perforation 30 for connecting the drug-support film-protecting cover. In addition, the protective cover 25 has a flat structure.

FIG. 15 is a diagram showing the electrode portion Ib used in Example 4, in which (a), (b), (c) and (d) are a view of the surface, a view of the interior, a view of the inner face and a cross sectional view of the electrode portion, respectively. As will be clear from this figure, the electrode portion is provided with a hole 21 for receiving the cup-shaped protective cover, an adhesive layer 22 (at the periphery of the hole for receiving the cup-shaped protective cover), a liner 23 for the adhesive layer (at the periphery of the hole for receiving the cup-shaped protective cover) and a perforation 24 for folding, at the hole for receiving the cup-shaped protective cover.

Figure 16A:
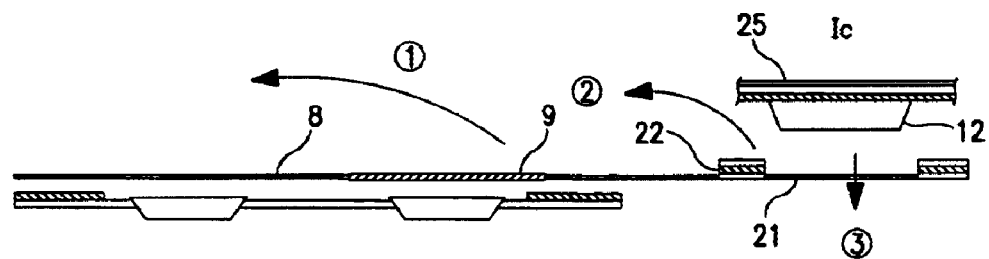
FIGS. 16(a) to (d) are diagrams for explaining a method for activating the iontophoresis device according to Example 4.
Figure 16B:
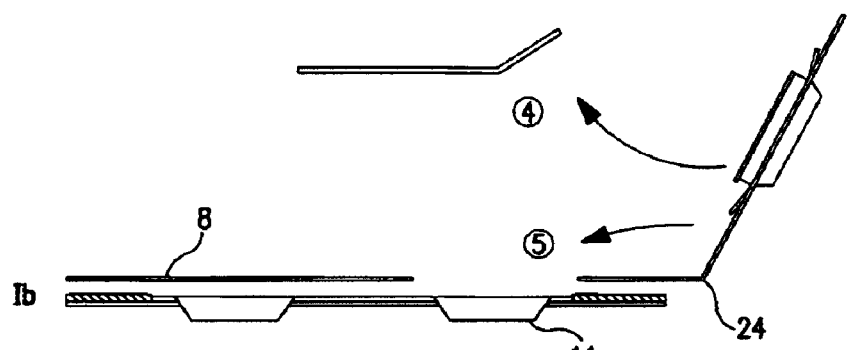
Figure 16C:
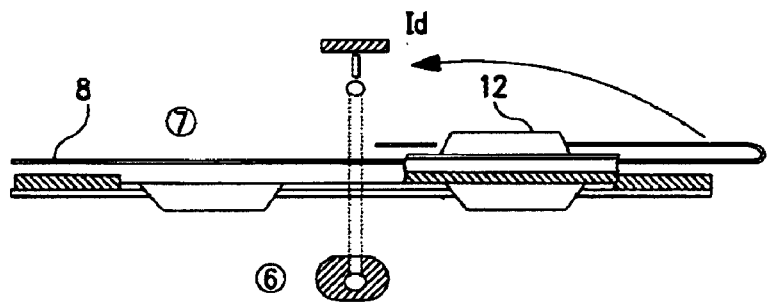

FIGS. 16(a) to (d) are diagrams for explaining the method for activating the iontophoresis device of Example 4. The activation procedures are as follows:

Operational Procedure (1): As shown in FIG. 16(a), a cover material 9 of the electrode portion Ib is released to thus expose the drug-dissolving portion 11.

Operational Procedures (2), (3): The cup-shaped protective cover 12 of the drug portion Ic is incorporated into the hole 21 for the cup-shaped protective cover positioned on the extension of the liner 8 for the adhesive film. Thus, the cup-shaped protective cover 12 is adhered and fixed to the hole 21 for the cup-shaped protective cover using the adhesive layer 22 at the periphery of the hole 21.

Operational Procedure (4): As will be clear from FIG. 16(b), the cover (flat cover) 25, on the electrode side, of the drug portion Ic is released and cut off along the perforation 30, for connection, of the drug-support film-protecting cover to thus remove the cover 25 on the electrode side.

Operational Procedure (5): The device is folded down at the boundary along the perforation 24 including the folding axis and formed on the liner 8 for the adhesive film, to bring the drug portion Ic into contact with the drug-dissolving portion 11 without any aberration of their positions and to thus integrally combine the drug-support film 14 of the drug portion with the drug-dissolving portion 11.

Operational Procedure (6): As will be seen from FIG. 16(c), separate and individual three portions, i.e., the current-generating portion Ia, the drug portion Ic and the electrode portion Ib are brought into contact with one another using the snap connector Id.

Figure 16D:
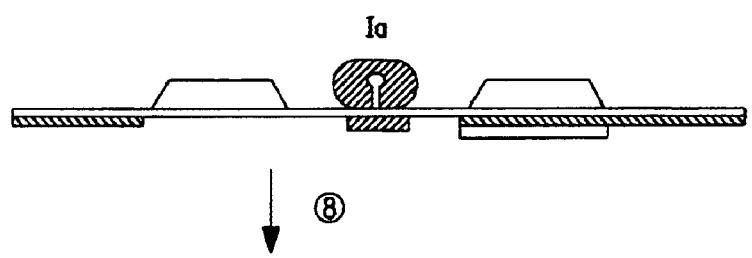
Figure 19A:
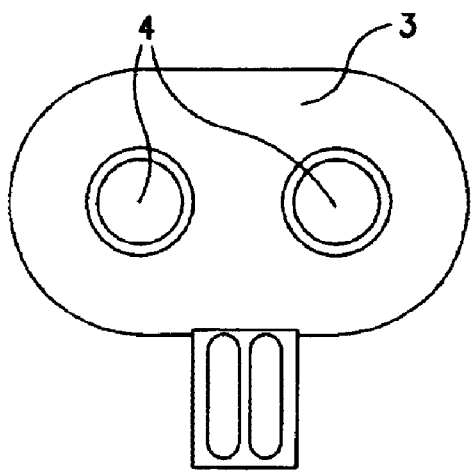
FIG. 19 is a diagram showing an electrode portion Ib used in Example 5, in which (a), (b), (c) and (d) are a view of the surface, an internal view, a view of the inner face and a cross sectional view of the electrode portion, respectively.
Figure 19B:
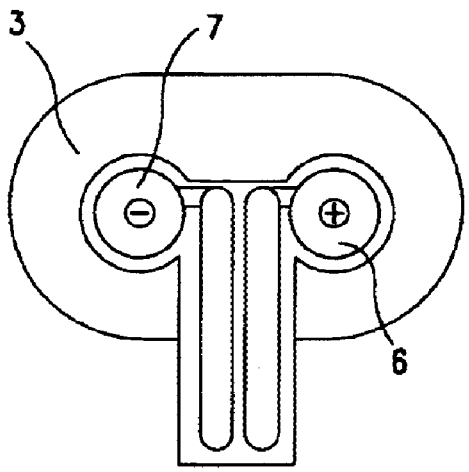
Figure 19C:
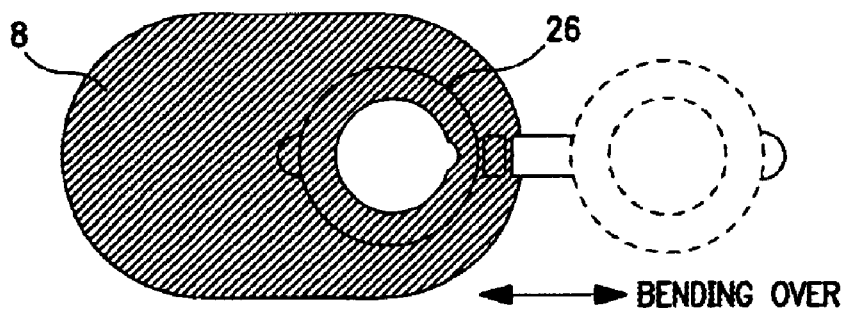
Figure 19D:
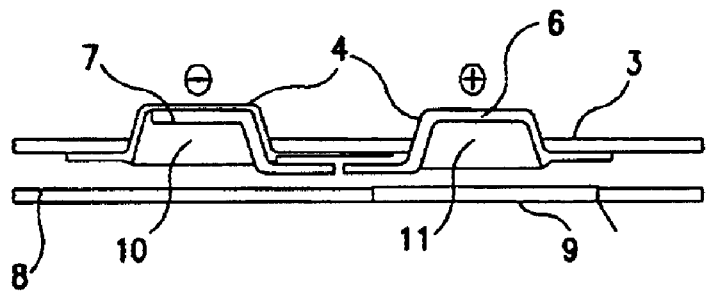
Figure 20A:
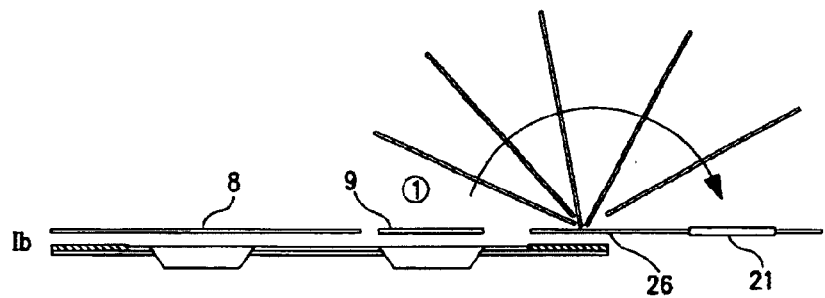
FIGS. 20(a) to (e) are diagrams for explaining a method for activating the iontophoresis device according to Example 5.
Figure 20B:
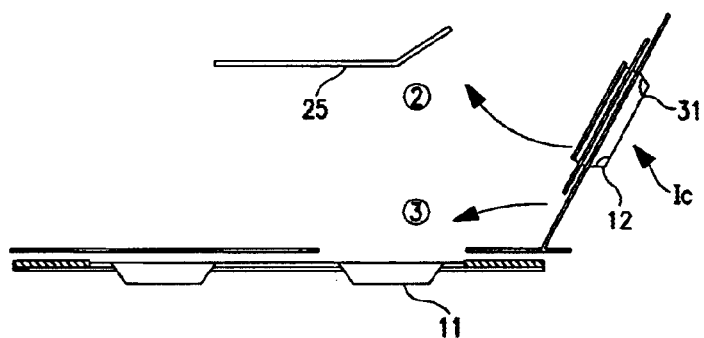
Figure 20C:
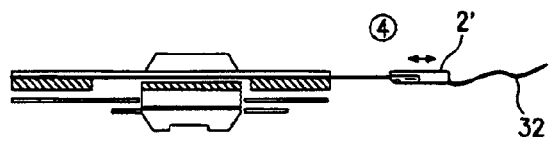
Figure 20D:
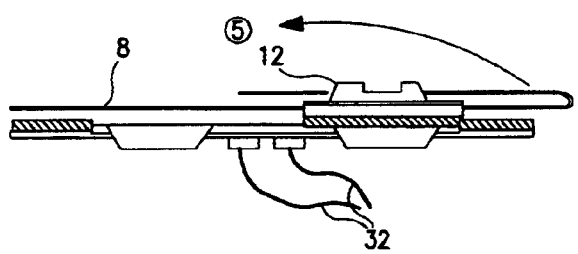
Figure 20E:
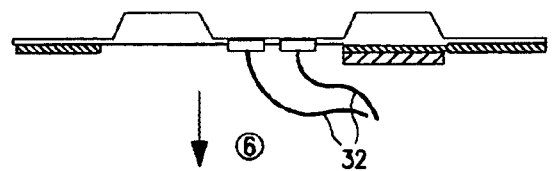

Operational Procedures ⑦, ⑧: The cup-shaped protective cover 12 of the drug portion and the liner 8 for the adhesive film are released immediately before the practical use of the device. Thus, as shown in FIG. 16(d), the device can be applied to the skin without any pre-treatment and the treatment of a patient can be initiated.

In this respect, the operational procedures for the activation of the device is not restricted to that described above and can be modified depending on the modes of application thereof to a patient and depending on various circumstances.

As has been described above, in the iontophoresis device according to Example 4, the cup-shaped protective cover 12 is fitted to the hole 21 for receiving the cup-shaped protective cover, formed on the extension of the liner 8 for the adhesive film and then the device is folded down along the perforation 24 formed on the liner 8 for the adhesive film. These operations permit the positioning of the drug portion Ic and the drug-dissolving portion 11. Therefore, the iontophoresis device of Example 4 can easily and precisely be activated upon application to the skin or mucous membrane. In addition, the device also permits the elimination of any artificial error as low as possible and precise supply, to the drug layer, of moisture required for re-dissolving the drug.

EXAMPLE 5

The iontophoresis device of Example 5 has a structure almost identical to that of the device according to Example 4, except that the hole 21 for cup-shaped protective cover is turned in the inside of the extension of the liner 8 for the adhesive film rather than the exterior thereof, by the perforation 26; that the electrode-charging portion Ia is designed in such a manner that it is provided with a current control/charging portion in addition to the application site, properly controls the current through a lead wire 32 and the terminal at the electrode portion is sandwiched by sliding the connected portion of the tip of the lead wire back and forth; and that the cup-like cover is molded and fabricated so that it can hold the drug-support film 14 therein and thus the drug-support film floats in the air, while the face thereof does not come in contact with the cover.

FIG. 17 is a diagram showing the drug portion Ic used in Example 5, in which (a), (b) and (c) are a top plan view of the drug-support film, a top plan view of the drug portion and a cross sectional view of the drug portion, respectively. As will be seen from this figure, the drug portion is provided with a drug-support film-protecting cover-molded and fabricated portion 31.

FIG. 18 is a diagram showing an embodiment in which the current-generating portion Ia is connected to the electrode portion Ib through the lead wire 32. In this embodiment, a connector 2' is connected to one end of the lead wire 32 and fixed to the electrode portion by sandwiching the electrode terminal. The other end of the lead wire 32 is connected to the current-generating portion Ia. If the lead wire 32 is used, the device can remotely be controlled.

FIG. 19 is a diagram showing the electrode portion Ib used in Example 5, in which (a), (b), (c) and (d) are a view of the surface, a view of the interior, a view of the inner face and a cross sectional view of the electrode portion, respectively. As will be clear from this figure, the electrode portion is provided with a perforation 26 at the hole for a concealed type cup-shaped protective cover.

FIGS. 20(a) to (e) are diagrams for explaining the method for activating the iontophoresis device according to Example 5. The activation procedures therefor are as follows:

Operational Procedure ①: As will be seen from FIG. 16(a), the hole for the cup-shaped protective cover, which is bent in a part (inside) of the liner 8 for the adhesive film, is outwardly folded along the perforation 26 at one edge thereof.

Operational Procedure ②: As will be clear from FIG. 20(b), the cup-shaped protective cover 12 of the drug portion Ic is incorporated into the hole 21 for receiving the cup-shaped protective cover, the cover (flat cover) 25 on the electrode side among the drug-support film-protecting covers is released, and cut off along the perforation including the folding axis at which the drug-support film-protecting cover is connected to the flat cover, to thus remove the cover 25 on the electrode side.

Operational Procedure ③: The cover material 9 of the electrode portion Ib is peeled off to thus expose the drug-dissolving portion. Then the molded cover is again folded back to the electrode side along the boundary or the perforation including the folding axis on the liner for the adhesive film, to thus press the molded and fabricated cover portion 31 for supporting the drug-support film of the cup-shaped protective cover 12 from the top thereof, to drop the drug-support film 14 within the cup, to bring the drug portion into contact with the drug-dissolving portion without causing any aberration of their positions and to thus combine the drug-support film 14 of the drug portion with the drug-dissolving portion 11.

Operational Procedure ④: As will be seen from FIG. 20(c), the current-generating portion Ia is connected to the electrode portion Ib by sliding the connector 2' at the tip of the lead wire 32 of the current-generating portion.

Operational Procedures ⑤, ⑥: As will be seen from FIGS. 16(d) and 16(e), the cup-shaped protective cover 12 of the drug portion and the liner 8 for the adhesive film are released immediately before the practical use of the device. Thus, the device can be applied to the skin without any pre-treatment and the treatment of a patient can be initiated.

In this respect, the operational procedures for the activation of the device is not restricted to that described above and can be modified depending on the modes of application thereof to a patient and depending on various circumstances.

As has been described above, the iontophoresis device according to Example 5 permits the reduction of the pharmaceutical preparation and makes the handling thereof easier, by incorporating the hole 21 for the cup-shaped protective cover of the drug portion Ic into the interior of the liner 8 for the adhesive film.

COMPARATIVE EXAMPLE 1

Figure 21A:
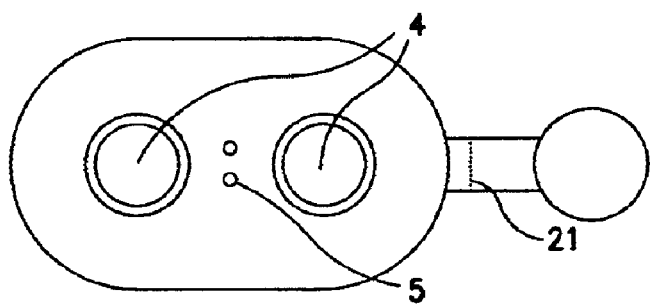
FIG. 21 is a schematic diagram showing an iontophoresis device according to Comparative Example 1, in which (a) is a view of the surface of the device, (b) is an internal view and a view of the back face thereof and (c) is a cross sectional view thereof.
Figure 21B:
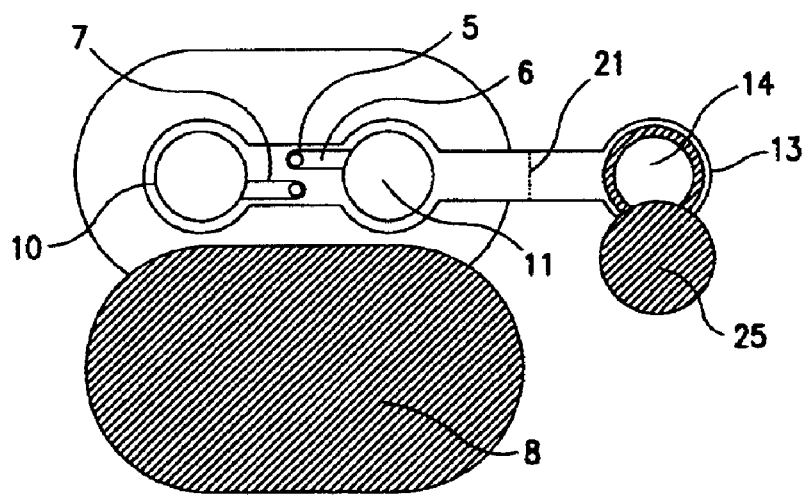
Figure 21C:
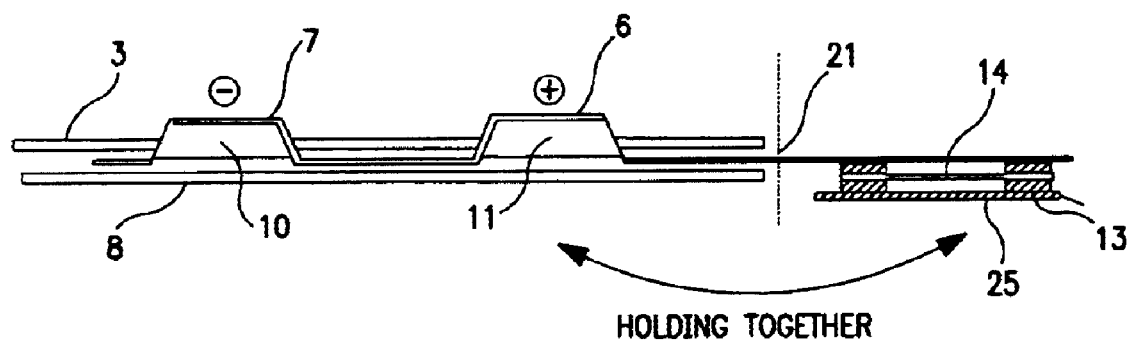

FIG. 21 is a diagram schematically showing an iontophoresis device according to Comparative Example 1, in which (a) is a view of the surface of the device, (b) is a view of the interior and a view of the back face of the device and (c) is a cross sectional view thereof. The iontophoresis device of Comparative Example 1 comprises an electrode portion and a drug portion, which are united through a backing and is so designed that liner layers of the electrode portion and the drug portion, which are connected to one another through a hinge system are released upon the practical application of the device and then these portions are folded up to thus activate the device. Incidentally, the internal structure is almost identical to that of the device according to Example 4.

TEST EXAMPLE 1

Determination of Blood Concentration of Salmon Calcitonin

In this Example, the following are newly prepared and used in respect of Example 3 and Comparative Example 1.

In Example 4 and Comparative Example 1, 1.0 g of a 1.5% agar gel containing a citric acid buffering solution (33 mM, pH 5) was introduced into the conductive layer adjacent to 2.5 cm² of a silver-printed portion (anode), while 1.0 g of sodium chloride-containing polyvinyl alcohol (UF-250G available from Unitika Ltd.) was introduced into a silver chloride-printed portion (cathode) to form an electrode portion. Moreover, a drug portion was prepared by dropwise addition of 20 IU of salmon calcitonin to 3.46 cm² of a drug-support film (BIODYNE+, available from Bole Company) and then drying the film.

After assembling or activating the iontophoresis devices provided with the parts thus produced, according to the procedures used in Example 4 and Comparative Example 1, each device was fitted to the abdominal region of an SD rat (body weight: 250 g) and the device was electrically charged by passing an electric current from the current-generating portion at a pulsed, depolarized voltage of 12 V, through a donor electrode as an anode and a reference electrode as a cathode. In this connection, four male persons each assembled or activated the iontophoresis devices of Example and Comparative Example. Sera were obtained by intrajugularly collecting blood from the rats with the elapse of time. The concentrations of salmon calcitonin in the sera were determined using a radioimmunoassay kit (Peninsula Salmon Calcitonin Quantitative Analysis Kit). The results thus obtained are plotted on FIG. 22.

Figure 22:
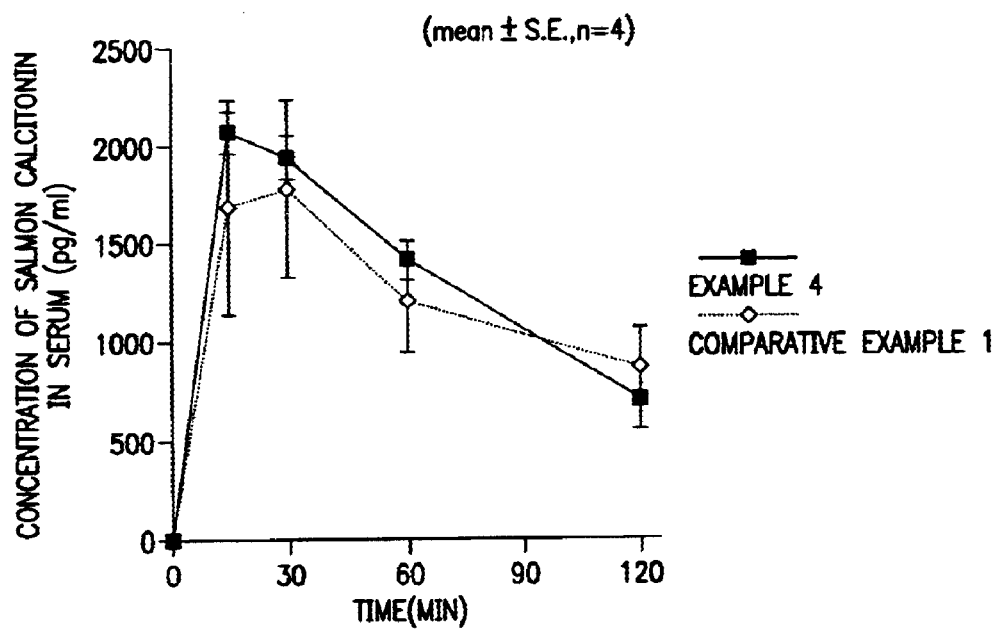
FIG. 22 is a graph showing changes, with time, of salmon calcitonin in the serum observed in Test Example 1.

As will be seen from the results shown in FIG. 22, the blood concentration of salmon calcitonin observed after 5 minutes were found to be 2075±108 pg/ml (averaged value± standard deviation) for Example 4 and 1867±548 pg/ml for Comparative Example 1. The tendency of the changes in the blood concentration observed for Example 4 and Comparative Example 1 were approximately identical to each other and there was not observed any significant difference therebetween. However, the blood concentration of salmon calcitonin observed for Comparative Example 1 varied widely as compared with that observed for Example 4 and there were observed adhesion of the drug solution to the flat liner surface after peeling in all of the 4 pharmaceutical preparations of Comparative Example, upon positioning of the drug portion and the drug-dissolving portion. This clearly indicates that the artificial errors upon the activation of the devices exert considerable influence on the blood concentration of salmon calcitonin.

Consequently, these results clearly indicate that the device of Example 4 makes the activating operations easy and precise when practically using the device and permits the elimination of any artificial error as much as possible and also permits the precise supply of moisture required for the dissolution of the drug to the drug support.

TEST EXAMPLE 2

Evaluation of Stability, With Time, of Salmon Calcitonin Incorporated Into Drug Portion The devices of Example 4 and Comparative Example 1 used in Test Example 1 were packaged under the following conditions and allowed to stand at 25° C., 65% R.H. to thus evaluate the stability, with time, of salmon calcitonin. In this Test Example, a composite aluminum packaging material (available from OKADA SHIGYO K. K.) and 1.0 g of OZO (available from OZO Chemical Co., Ltd.) were used as the packaging agent and the drying agent, respectively. The results thus obtained are plotted on FIG. 23.

Figure 23:
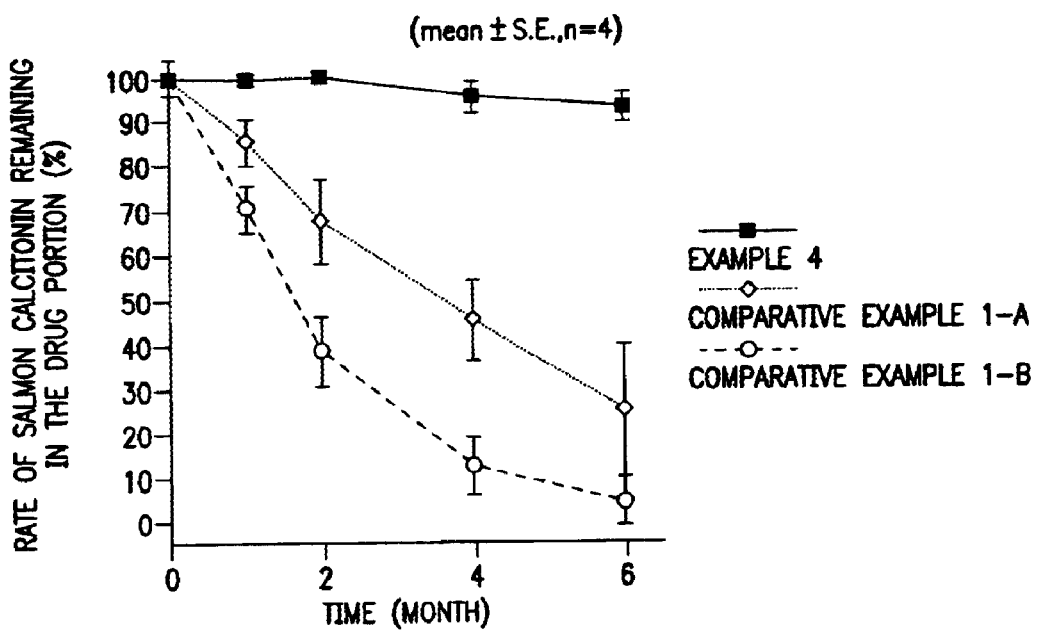
FIG. 23 is a graph showing changes, with time, of the rate of the salmon calcitonin remaining in the drug portion, observed in Test Example 2.

The results plotted on FIG. 23 indicate that, when the water containing electrode portion and the drug portion in a dried condition are packed in the same package, the former adversely affects the stability, with time, of the drug in the drug portion (Comparative Example 1-B in FIG. 23). In addition, when the electrode and drug portions are packed in the same package and a drying agent is used therein, the drug stability is improved to some extent, but it was found, in one out of four cases, that the water in the electrode portion was exhausted after allowing it to stand over 6 months (Comparative Example 1-A in FIG. 23). On the other hand, the drug exhibited quite excellent stability in the device of Example 4.

From the foregoing, it would be recognized that it is practically difficult to ensure the long-term stability of a drug using a device provided with integrated electrode and drug portions. Moreover, in case of a device provided with electrode and drug portions separated from one another, a drying agent may be used and therefore, the long-term stability of a drug would further be improved.

From the foregoing, the iontophoresis device according to the present invention exhibits excellent pharmaceutical effect and permits the achievement of an improved compliance of patients. Moreover, the device can ensure sufficient safety in both operations and functions and thus has high reliability.

Industrial Applicability

The iontophoresis device according to the present invention is effective for ensuring the long-term stability of a drug and the method for assembling the device according to the present invention is advantageous in that the device can easily be assembled. Therefore, the present invention is suitably used for the iontophoresis in the medical field.

What is claimed is:

1. An iontophoresis device in which a drug portion is brought into contact with a drug-dissolving portion upon practical use to thus administrate a drug supported by the drug portion, wherein the drug portion comprises a drug-support for supporting the drug and covers, which do not come in contact with the drug-support, for protecting both sides of the drug-support, and at least one of the drug-support and the covers is subjected to fabrication treatment for positioning.

2. The iontophoresis device according to claim 1 wherein at least one of the covers is molded and fabricated into a cup-like shape.

3. The iontophoresis device according to claim 1 wherein the drug-support is a porous polymer film.

4. The iontophoresis device according to claim 1, wherein the drug-support is obtained by applying a drug solution and then drying.

5. The iontophoresis device according to claim 1, wherein one of the covers has a hole for applying the drug solution.

6. The iontophoresis device according to claim 1, wherein at least one of the covers is coated with silicone.

7. The iontophoresis device according to claim 1, wherein an adhesive layer is arranged on the periphery of both of the sides of the drug-support.

8. The iontophoresis device according to claim 1, wherein it is further provided with an additional structure for positioning the drug portion and the drug-dissolving portion.

9. The iontophoresis device according to claim 8, wherein the additional structure is a hole for positioning, arranged on the periphery of at least one of the drug portion and the drug-dissolving portion.

10. The iontophoresis device according to claim 8, wherein the additional structure is a hole formed on a part of a release cover for the drug-dissolving portion and capable of being combined with the drug portion.

11. The iontophoresis device according to claim 8, wherein a concave or convex frame is formed on the periphery of the drug-dissolving portion and the cup portion is incorporated into the frame to perform the positioning of the drug-dissolving portion and the drug portion.

12. The iontophoresis device according to claim 8, wherein the periphery of the drug portion is molded and fabricated into a concave or convex shape, the drug-dissolving portion is provided with a concave or convex molded portion at the corresponding position and the concave and convex portions of the drug portion, and the drug-dissolving portion are combined together to thus perform the positioning of these portions.

13. The iontophoresis device according to claim 8, wherein the cup portion of the drug portion is molded and the positioning of the drug-dissolving portion and the drug portion is performed by pressing the cup portion from the top thereof.

14. A drug unit comprising a drug-support for supporting a drug and covers arranged on both sides of the drug-support while the covers do not come in contact with the drug support, said covers having a cup-like shape with an opening for applying a drug.

15. A kit for an iontophoresis device comprising an electrode portion provided with a drug-dissolving portion and a drug portion, which comprises a drug-support for supporting a drug and covers arranged on both sides of the drug-support while the covers do not come in contact with the drug-support, wherein the drug portion and the electrode portion are accommodated in separate packages.

16. The kit for an iontophoresis device according to claim 15, wherein the electrode portion and the drug portion are subjected to positioning treatments for laminating these portions.

* * * * *